United States Patent [19]

Nazarian et al.

[11] Patent Number: 5,614,670

[45] Date of Patent: Mar. 25, 1997

[54] MOVABLE SEISMIC PAVEMENT ANALYZER

[75] Inventors: Soheil Nazarian; Mark R. Baker; Kevin Crain, all of El Paso, Tex.

[73] Assignee: Board of Regents, The University of Texas System, Austin, Tex.

[21] Appl. No.: 674,460

[22] Filed: Jul. 2, 1996

Related U.S. Application Data

[63] Continuation of Ser. No. 145,996, Oct. 29, 1993, abandoned.

[51] Int. Cl.$^6$ ........................................... E01C 23/00
[52] U.S. Cl. ................................... 73/146; 73/8
[58] Field of Search ............................ 73/146, 8

[56] References Cited

U.S. PATENT DOCUMENTS

| Re. 27,875 | 1/1974 | Swift . | |
|---|---|---|---|
| 3,888,108 | 6/1975 | Brands | 73/146 X |
| 4,008,784 | 2/1977 | Bays . | |
| 4,341,282 | 7/1982 | Bird . | |
| 4,473,319 | 7/1984 | Spangler | 73/146 X |
| 4,700,331 | 10/1987 | Scott . | |
| 4,881,405 | 11/1989 | Paquet . | |
| 4,887,463 | 12/1989 | Wood . | |
| 4,985,306 | 9/1990 | Powell et al. . | |
| 5,325,701 | 7/1994 | Zilliacus | 73/12.04 |

OTHER PUBLICATIONS

Nazarian et al., "Nondestructive Evaluation of Pavements bySurface Wave Method," STP 1026, American Society for Testingand Materials, Philadelphia, pp. 119–137.
Ameri–Gaznon, M., and D. N. Little, "Permanent Deformation Potential in Asphalt Concrete Overlay Over Portland Cement Concrete Pavements," *Research Report 452-3F, Texas Transportation Institute, College Station, TX* (1988).
Bell, C. A, "Summary Report on the Aging of Asphalt–Aggregate Systems," *Report SHRP–A/IR–89–004. Strategic Highway Research Program, National Research Council, Washington, DC* (1989).
Carpenter et al., "A Pavement Moisture Accelerated Distress Identification System—vol. 2: User's Manual," *Research Report FHWA–RD–81–080. Federal Highway Administration, U.S. DOT, Washington, DC.* (1981).
Cedergren, H. R., *Drainage of Highway and Airfield Pavements*, ch. 1, pp. 1–22 (1987).
Cooley, J.S. and Turkey, J.W., "An Algorithm for the Machine Calculation of Complex Fourier Series," *Mathematics of Computation*, vol. 19, pp. 223–227 (1965).
Dobry, R., and G. Gazetas. "Dynamic Response of Arbitrary Shaped Foundations," *Journal of Geotechnical Engineering (American Society of Civil Engineers, New York)*, vol. 2, pp. 109–135 (1986).
Goodrich, J. L., "Asphalt and Polymer Modified Asphalt Properties Related to Performance of Asphalt Concrete Mixtures," *Proceedings, Association of Asphalt Paving Technologists* vol. 57, pp. 116–175 (1988).

(List continued on next page.)

*Primary Examiner*—Hezron E. Williams
*Assistant Examiner*—Joseph L. Felber
*Attorney, Agent, or Firm*—Arnold, White & Durkee

[57] ABSTRACT

A device and method for monitoring conditions associated with pavement deterioration are disclosed. Conditions such as voids or loss of support under a rigid pavement, moisture infiltration in asphalt concrete pavement, fine cracking in pavements, delamination of overlays, and aging of asphalt may be measured according to the present invention. These pavement conditions are detected by estimating Young's and shear moduli in the pavement, base, and subgrade from the following wave propagation measurements: Impact Echo; Impulse Response; Spectral Analysis of Surface Waves; Ultrasonic Surface Wave; and Ultrasonic Body Wave Velocity. The pavement response produced by high- and low-frequency pneumatic hammers on five accelerometers and three geophones is recorded. A computer controls data acquisition, instrument control, and interpretation; measurements and interpretations are reported in both screen and database formats.

13 Claims, 24 Drawing Sheets

OTHER PUBLICATIONS

Maser, K. R. and M. J. Markow, "Measuring Systems and Instrumentation for Evaluating the Effectiveness of Preventive Maintenance," *Report SHRP-M/UWP-91-513, Strategic Highway Research Program, National Research Council, Washington, DC* (1991).

Nazarian, S. and Baker, M., "A New NDT Device Under Development for Preventive Pavement Maintenance," *Technical Quarterly*, No. TQ7-3, pp. 1-6 (Sep., 1992).

Nazarian, S. and Desai, M., "Automated Surface Wave Testing: Field Testing," *Journal of Geotechnical Engineering*, vol. 119, pp. 1094-1112 (1993).

Nazarian, S., Reddy, S. and Baker, M., "Determination of Voids Under Rigid Pavements Using Impulse Response Method," *Nondestructive Testing of Pavements and Backcalculation of Moduli (Second Volume), ASTM STP* 1198, American Society for Testing and Materials (Harold L. Von Quintas, Albert J. Bush, and Gilbert Y. Baladi, Eds., 1994).

Reddy, S., "Determination of Voids in Rigid Pavements Using the Impulse Response Method," *M.S. Thesis, The University of Texas at El Paso, El Paso* (1992).

Richardson, M. H., and D. L. Formenti, "Parameter Estimation from Frequency Response Measurements Using Rational Fraction Polynomials," *Proceedings, First International Modal Analysis Conference (Society for Experimental Mechanics, Orlando, FL)*, pp. 167-181 (1982).

Rodhe, G. et al., "User's Guide to the Texas Flexible Pavement System (TFPS) Program," Research Report No. 455-2, *Texas Transportation Institute, College Station, TX* (Oct. 1991).

Tia, M. et al., "Investigation of Original and In-Service Properties for Development of Improved Specifications: Final Phase of Testing and Analysis," *Final Report. Engineering and Industrial Experiment Station, University of Florida, Gainsville, FL* (1988).

Torres, F., and B. F. McCullough, "Void Detection and Grouting Process," *Research Report* 249-3, *Center for Transportation Research, The University of Texas, Austin, TX* (1983).

Uzan, J., Zollinger, D.G., and Lytton, R.L., "Mechanistic/Empirical Model for the Structural Design of Flexible Pavement," *Report for Research Project* 455-1, *Texas Transportation Institute, Texas A&M University, College Station, TX*, Ch. 1, pp. 1-29 (Nov. 1991).

Von Quintus, H. et al., "Asphalt Aggregate Mixture Analysis System," *Report* 338 (*National Cooperative Highway Research Program, National Research Council, Washington, DC*), (Mar. 1991).

Willis, M. and Toksöz, M., "Automatic P and S Velocity Determination from Full Waveform Digital Acoustic Logs," *Geophysics*, vol. 48, pp. 1631-1644 (Dec. 1983).

Yuan, D. and Nazarian, S., "Automated Surface Wave Method Inversion Technique," *Journal of Geotechnical Engineering*, vol. 119, pp. 1112-1126 (1993).

Brochure: "Project Level Maintenance Measuring Equipment: The Surface Analyzer," *Strategic Highway Research Program, National Research Council.* This brochure was publicly distributed by the Strategic Highway Research Program in or about Oct., 1991 and by the American Association of State Highways and Transportation Officials (AASHTO) during its Annual Meeting and Exhibition in Milwaukee, Wisconsin in Oct., 1991.

A photograph of a first pre-prototype of the device exhibited at the AASHTO Annual Meeting in Milwaukee, Wisconsin in Oct., 1991.

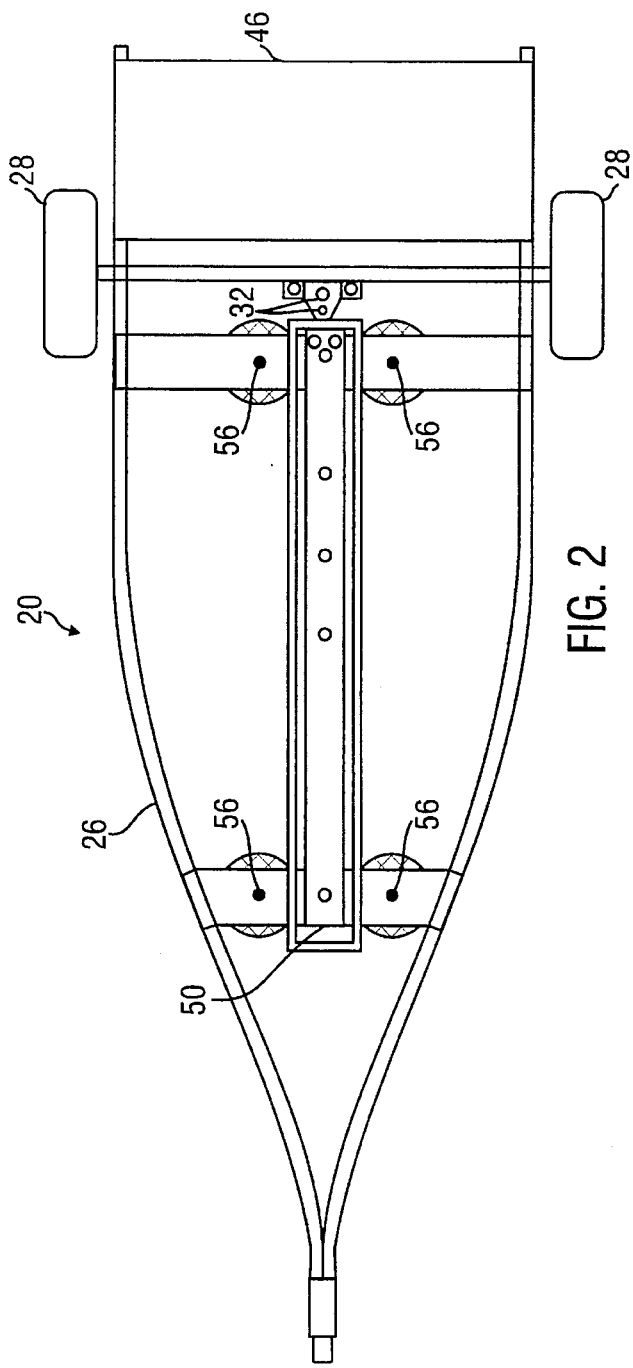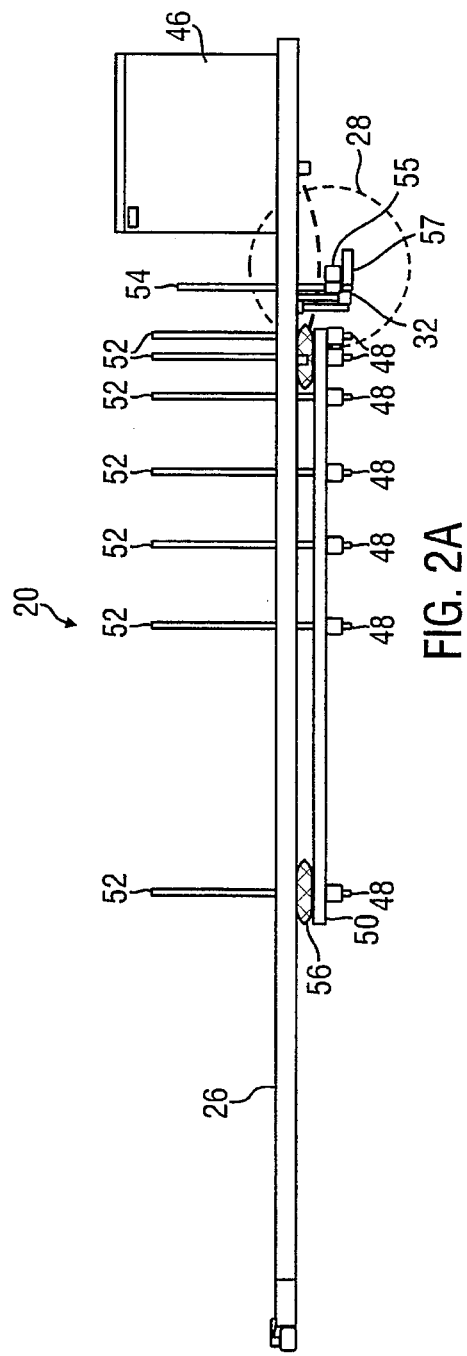

MOVABLE SEISMIC PAVEMENT ANALYZER

This application is a continuation of application Ser. No. 08/145,996, filed Oct. 29, 1993 now abandoned.

BACKGROUND OF THE INVENTION

In recent years, the focus of pavement engineering has shifted from design and construction of new highways to preventive maintenance and rehabilitation of the existing highways. A highway maintenance program is usually based on a visual condition survey and, to a lesser extent, on appropriate in situ tests. By the time symptoms of deterioration are visible, major rehabilitation or reconstruction is often required. If the onset of deterioration can be measured accurately in the early stages, the problem can often be resolved or stabilized through preventive maintenance.

The Strategic Highway Research Program has identified six broad elements that cause and contribute to pavement deterioration, as discussed in Maser, K. R. and M. J. Markow, "Measuring Systems and Instrumentation for Evaluating the Effectiveness of Preventive Maintenance," *Report SHRP-MIUWP*-91-513, *Strategic Highway Research Program, National Research Council, Washington, D.C.* (1990), the disclosure of which is herein incorporated by reference:

1. Pavement moisture;
2. Subsurface problems or discontinuities;
3. Voids or loss of support under rigid pavements;
4. Overlay delamination;
5. Fine cracking; and
6. Asphalt aging.

A. Pavement Conditions

1. Moisture in the Foundation

The types of distress caused by moisture-related problems in the foundation layers (in advanced stages) are summarized by Carpenter et al., "A Pavement Moisture Accelerated Distress Identification System—Volume 2: User's Manual," *Research Report FHWA-RD*-81-080 *Federal HighWay Administration, U.S. DOT, Washington, D.C.* (1981), the disclosure of which is herein incorporated by reference. Typically, the softening of one or more of the foundation layers and the degradation of material quality in terms of stiffness and strength are the initial manifestations of excess moisture within the pavement system. Field studies have shown that wheel loads on saturated sections are many times more damaging than those on dry sections. See Cedergren, H. R., *Drainage of Highway and Airfield Pavements* (1974), the disclosure of which is herein incorporated by reference.

2. Moisture Under Joints

The deterioration of foundation layers exposed to moisture in a rigid pavement is similar to that in a flexible pavement. Erodible foundation materials under a slab will deteriorate when subjected to load. The existence of moisture significantly increases the rate of deterioration. In this case, the foundation layer will either become softer or a void will develop under the concrete slab. Slab curling (bending or warping) will contribute to the deterioration.

3. Voids or Loss of Support

The presence of voids or loss of support underneath a slab of rigid pavement is detrimental because it causes increase in stresses in pavement, decrease in the fatigue life of the pavement, and a possibility for faulting of joints. Important factors in this process are discussed by Torres, F., and B. F. McCullough, "Void Detection and Grouting Process," *Research Report* 249-3, *Center for Transportation Research, The University of Texas, Austin, Tex.* (1983), the disclosure of which is herein incorporated by reference. The larger the void or the thinner the slab, the lower the support and the shorter the life of the pavement.

4. Overlay Delamination

The process and significance of overlay delamination is well known. The degree of interfacial bonding influences the state of stress within the overlay. Interfacial bonding has been identified as the most significant factor affecting overlay performance. See Ameri-Gaznon, M., and D. N. Little, "Permanent Deformation Potential in Asphalt Concrete Overlay Over Portland Cement Concrete Pavements," *Research Report* 452-3F, *Texas Transportation Institute, College Station, Tex.* (1988), the disclosure of which is herein incorporated by reference. When delaminated, the overlay acts independently of the rest of the pavement system, allowing excessive movement at the bottom of the overlay relative to the top, where the wheel load is in contact with the pavement. As a result, large tensile strains develop at the bottom of the overlay.

5. Fine Cracking

Cracks often begin as hairline cracks that allow little water into the structure. Although they are a discontinuity in the pavement structure, they are not generally a problem until they become wide enough to allow water to enter into the structure. If allowed to deteriorate, they become wider, allowing much more water to enter. Furthermore, the intrusion of an incompressible material during a cold period creates high compressive forces on the crack or joint face during warmer periods, creating spalling. The cracks may also contribute to the aging process of asphalt on the crack face, accelerating crack deterioration.

6. Pavement Aging

The aging process in the field is complex. Several independent investigations have indicated that the stiffness of the asphalt in a flexible paving layer increases with time (aging). See Tia, M. et al., "Investigation of Original and In-Service Properties for Development of Improved Specifications: Final Phase of Testing and Analysis," *Final Report. Engineering and Industrial Experiment Station, University of Florida, Gainsville, Fla.* (1988); Goodrich, J. L., "Asphalt and Polymer Modified Asphalt Properties Related to Performance of Asphalt Concrete Mixtures," *Proceedings, Association of Asphalt Paving Technologists* vol. 57, pp. 116-75 (1988); Von Quintus, H. et al., "Asphalt Aggregate Mixture Analysis System," *Report* 338 (*National Cooperative Highway Research Program, National Research Council, Washington, D.C.*) (1991), the disclosures of which are herein incorporated by reference. It has further been suggested that aging should be considered in two stages: short-term and long-term. See Bell, C. A, "Summary Report on the Aging of Asphalt-Aggregate Systems," *Report SHRP-A-305. Strategic Highway Research Program, National Research Council, Washington, D.C.* (1989), incorporated herein by reference. Short-term aging occurs during construction, while the mix is hot. Such aging is mainly due to a loss of volatile components in the asphalt. Long-term aging occurs after the mixture is in place, and is primarily attributed to progressive oxidation of the material in the field.

B. Maintenance Activities

A device capable of detecting the foregoing elements early is desirable for preventive maintenance. Four major features in such a measurement device are necessary for effective maintenance measurements. First, the device should be sensitive enough to measure a contributing factor to a potential distress "soon enough." Second, the measurements should be accurate and comprehensive enough to identify the layer contributing to a potential distress. Third, the device should be precise enough to verify the effectiveness of maintenance processes. Finally, the device should be sophisticated enough to differentiate between a rehabilitation activity and a maintenance activity. Rehabilitation includes complete or partial replacement of the pavement layer, whereas maintenance involves fixing (e.g., patching) a more localized defect prior to total tiff lure. By way of analogy, pavement rehabilitation is to pavement maintenance as fitting dentures is to filling a cavity. Generally, maintenance is less expensive than rehabilitation.

The maintenance activities discussed herein are those that correct a localized area of deterioration, preserve the existing pavement, and reduce the rate of deterioration (e.g., corrective and preventive maintenance). Treatments that fall within this category of maintenance are included in Table I for two common types of road surfaces: Asphaltic concrete and Portland cement concrete. In general, these treatments do not increase the structural or traffic-handling capacity of the roadway.

TABLE I

Treatments that Are Considered Maintenance

| Asphaltic-Concrete Roads | Portland-Cement Concrete Roads |
|---|---|
| Patching | Patching |
| Crack Sealing or Filling | Joint Repair |
| Surface Sealing | Crack and Joint Sealing |
| (all types) | Undersealing |

Each of these activities addresses specific problems in the pavement structure. To determine when to apply a maintenance treatment and which treatment is appropriate, the maintenance engineer tries to answer several questions. Does this section of pavement need a treatment now? If not, will it need one in the near future (less than three years)? Is the problem localized, or does it cover a large area? Which treatment should be applied? Is the treatment cost effective?

1. Patching

Patching is the repair of localized areas of low strength or other types of deterioration. Patching can address every possible type of deterioration, but only if the damage is localized. Such distress can occur in any pavement layer, leading to a localized failure observable on the surface. Loss of strength can be caused by a change in the material properties or localized differences in construction and original materials. It can also be due to loss of support caused by erosion or degradation of supporting layers.

Maintenance engineers typically do not test to determine if patching is required. They simply begin applying patches when the deterioration affects the pavement surface to the point that driving becomes hazardous. The key question that a maintenance engineer needs to address in testing is whether patching will effectively resolve the problem. If the problem is widespread, a comprehensive rehabilitation treatment will be more cost effective than patching.

2. Crack and Joint Sealing

Many of the materials used in pavement construction have moisture-sensitive stiffness. As the moisture content of unbound granular materials and soils increases, their stiffness decreases. Moisture leads to the degradation of asphalt concrete due to stripping, aging, weathering, and raveling. Free water under Portland cement slabs can develop very high pressures, eroding the base and subbase materials, or leading to loss of support. Crack and joint sealing help to prevent such deterioration by reducing the influx of moisture from the surface into the pavement structure.

A typical maintenance engineer will generally use the observable condition of the crack and joints to determine if crack and joint sealing is appropriate. Many maintenance engineers will not seal a crack until it is greater than 5 mm wide. If the amount of weakening resulting from moisture at the joints and cracks could be determined, that information could help determine when crack and joint sealing is needed to reduce the infiltration of moisture.

3. Surface Seals

Surface seals generally extend the life of pavements by improving the surface friction of the pavement, by reducing weathering and raveling, or by reducing the infiltration of moisture into the pavement structure.

The maintenance engineer normally looks for signs of weathering and raveling or for the presence of a network of fine cracks that can be sealed with the surface seal. If the presence and level of aging could be determined, the degradation of asphalt because of aging could be prevented or reduced. If the degradation of paving materials because of abnormal moisture levels in the asphalt and supporting layers or fine cracking could be determined, the need to place a seal to reduce infiltration of water into the structure could be evaluated.

4. Undersealing

Undersealing is the process of filling voids under Portland cement concrete pavements with a grout of cementatious material in order to reestablish support under the slab. The movement and loss of fine-grained materials creates voids, normally on the leave side of the joint or crack. This leads to faulting of the joint or crack. The loss of support also increases the stress in the Portland cement concrete pavement near the corners, leading to corner breaks.

In some cases, the base material is degraded but not ejected. This can create a thin layer of very soft material under the joint. A loss of support is then present without a true void. In such a case, undersealing generally cannot displace the deteriorated materials sufficiently to reestablish full support.

A maintenance engineer typically looks for the presence of pumping, faulting, and corner breaks to determine that voids are present and to determine if undersealing is appropriate. In some instances, nondestructive testing devices (such as falling weight deflectometer and Dynaflect) or manual methods (such as dropping a BB) are used for this task. Measurements to determine the loss of support, the presence of voids, and the size of voids are needed to determine if voids are developing and if undersealing should be considered to reestablish support.

C. Developing Specifications for Measurement

It is extremely important to measure the precursors of distress in the early stages. Below a certain measurement level, a change in the distress-triggering parameters results in insignificant changes in the condition or serviceability of the pavement. However, if the precursors of distress are identified "too late," reconstruction or rehabilitation may be more appropriate.

The remaining life of a pavement is controlled by the complex interaction of several factors such as traffic, pavement structure, drainage, road geometry, climate, and economy. In recent years, several methods have been developed to predict the type and rate of deterioration and to suggest alternative maintenance strategies at appropriate time intervals.

An example of a maintenance method is the Texas Flexible Pavement System (TFPS), described in Uzan, J., and R. E. Smith, "TFPS Technical Report," *Draft Report for Research Project 455, Texas Transportation Institute, Texas*

A&M University, College Station, Tex. (1988), and Rodhe, G. et al., "User's Guide to the Texas Flexible Pavement System (TFPS) Program," *Texas Transportation Institute, College Station, Tex.* (1990), the disclosures of which are herein incorporated by reference. In ideal conditions, one can adhere to these "theoretical" maintenance schedules. Often, however, pavements experience distress prematurely or maintenance activities are ineffective.

Cracking and moisture in the foundation are considered together because of the strong interaction that exists between them. The paving layer of a new pavement (which comprises a top layer, a base, and, optionally, a subbase, on top of a subgrade) is usually impervious, and cracks are scarce or nonexistent. In this stage, most of the damage to the pavement is the result of traffic or environment, and moisture infiltrates either from the shoulders or from the water table. As soon as cracks develop, moisture may penetrate from the surface. If the surface layer is primarily a wearing course and the majority of the structure is in the base, the infiltration of moisture and the existence of cracks are not of great concern so long as the base and subgrade materials do not lose their integrity because of exposure to moisture.

The TFPS considers the effects and interactions of several parameters in a comprehensive fashion. Factors that are considered (excluding political and economic factors) include the climatic parameters (such as the amount and seasonal distribution of rainfall), the drainage properties of the base and subgrade materials, the structural properties of the asphalt concrete, base, subgrade, and their seasonal variations, and the nature and seasonal distribution of traffic. The amount and seasonal distribution of the rainfall are modeled from the historical data from each county in the State of Texas. Based upon these climatic models, the properties of each layer are regularly modified and updated.

The parameters that the TFPS considers include moisture, temperature, and distress type; however, the TFPS program does not consider the transient and dynamic nature of change in moisture or stiffness with time. Considering the most basic principles of geotechnical engineering, the transient and dynamic nature of change in moisture is of little practical use in predicting maintenance life. A material that becomes saturated and unsaturated over a short time period is a well-drained material and has high permeability. The strength and stiffness of such a material (and as a result, the remaining life of a pavement constructed with or over such a material) is not significantly affected by change in moisture. On the other hand, in a material that does not exhibit large fluctuation in moisture over short periods (i.e., a material with low permeability), the change in equilibrium base moisture may significantly affect its stiffness and remaining life.

Thus, a shortcoming of TFPS, as applied to maintenance problems, is that it does not model the accumulation of damage resulting from change in equilibrium base moisture or stiffness.

In summary, maintenance engineers have typically relied on visible distress, along with pavement age and traffic levels, to schedule preventive or corrective maintenance. Preventive maintenance usually costs only a fraction of the expense of major corrective maintenance. However, successful preventive maintenance requires diagnosing pavement distress at its earliest stages. Objective engineering information on this sort of "distress precursor" has not been readily available, in part due to the difficulty of measuring pavement damage at early stages. Thus, a need exists for a reliable system to nondestructively test pavement for the presence of visible as well as invisible distress precursors and to determine when and what sort of preventive maintenance is needed.

SUMMARY OF THE INVENTION

The apparatus of the present invention broadly comprises a nondestructive measurement device called the Seismic Pavement Analyzer (SPA), which is an effective tool for determining pavement distress precursors (visible and invisible) in early stages. The device according to the present invention comprises a mobile support unit or trailer that may be towed behind a vehicle. Coupled to the trailer are at least two pneumatic seismic sources—a low-frequency (subsonic) source, and a high-frequency (ultrasonic) source. A tonal head may be coupled to each source to control the frequency input to the pavement. A plurality of transducer-receivers is also coupled to the trailer, including accelerometers located at five distances from the high-frequency source, and geophones located at three distances from the low-frequency source. The sources and transducers are lowered to and raised from the pavement by pneumatic cylinders that are controlled by a computer. The computer may be coupled to the trailer, or operated remotely from the trailer. Within the computer are data acquisition hardware, signal conditioning units, feedback control, multiplexer and gain control, and other electronic components.

The basic operation is as follows. The operator initiates the computer-controlled measurement cycle. The computer then lowers the sources and transducers to the pavement. The sources are fired as appropriate for the particular test or tests to be conducted, as described below. The transducers receive the transmitted seismic waves and convert those energy waves to electrical signals that are then fed to the computer for processing. Through a series of computations, the computer processes the signals. Diagnostic software is also included for diagnosing particular distress precursors based on the processed data.

Five distress precursors are addressed in the present invention:
1. Moisture in the base layer (flexible pavement);
2. Voids or loss of support under joints (rigid pavement);
3. Overlay delamination;
4. Fine cracking; and
5. Pavement aging.

Effective measurement of pavement conditions that are precursors to distress requires measuring a large number of pavement properties. As the distress precursors identified in previous sections are not directly measurable physical properties, several physical property measurements must be made to diagnose the precursors.

The operating principle of the SPA is based on generating and detecting stress waves ( seismic waves ) in a layered medium. Several seismic testing techniques are combined in the preferred apparatus and method of the present invention:
1. Ultrasonic Body Wave;
2. Ultrasonic Surface Wave;
3. Impulse Response;
4. Spectral Analysis of Surface Waves (SASW); and
5. Impact Echo.

The principles of these basic measurement techniques are outlined below.

The design and construction of the SPA are based on two general principles. First, the area of strength of each of the five testing methods should be fully utilized. Second, testing should provide enough redundancy to identify each sublayer of the paving layer that will potentially contribute to the distress of the pavement.

To diagnose the specified distress precursors effectively, it is preferred that a number of independent pavement parameters equal to the number of distress types be used. This large number of parameters may be measured with equipment similar to a falling weight deflectometer, but preferably using more sophisticated computer processing and interpretation methods as described herein.

The potential savings to be realized through use of the device and method of the present invention are tremendous. First, having detected and measured an early precursor of distress, a highway agency can resolve potential problems with preventive maintenance at a fraction of the cost of traditional maintenance or rehabilitation processes. In other words, the SPA can tell when is the best time to undertake a maintenance activity. Second, the device will enable the maintenance engineer to distinguish between maintainable sections and those that actually require rehabilitation. Therefore, the available maintenance funds can be directed toward maintainable projects. Third, the SPA can identify exactly which layer requires maintenance, avoiding costly guesswork. Fourth, the device can determine the effectiveness of a certain maintenance activity. Finally, based on the foregoing information, pavement design practices can be modified to optimize future maintenance activities.

Thus, the device of the present invention can perform several functions:

1. Analyze in greater detail pavement conditions identified in the network-level surveys;
2. Diagnose specific distress precursors to aid in selecting the maintenance treatment; and
3. Monitor pavement conditions after maintenance to determine the treatment's effectiveness.

The system is preferably automated to make its operation simple. For example, in an automated system, most of the data reduction may be done rapidly in the field, saving the results in a database for later analysis. An on-demand graphical representation of the data collected in the field can enable the engineer to identify troublesome areas within seconds of collecting the data. Then, diagnostic software can present the diagnosis of pavement conditions in literal pavement terms, as opposed to technical engineering terms (such as stiffness parameters).

The device of the present invention has several advantages over the prior art. The SPA is highly accurate in determining the present condition of the pavement. It uses methodology based on a sound theoretical background. The field testing and data reduction methodologies are compatible with the theoretical assumptions. The hardware associated with the device is relatively inexpensive. Further upgrade of the device should be inexpensive, because generally only the software will need to be updated and replaced.

A. Wave Propagation Theory

For engineering purposes, profiles of most pavement sections can be reasonably approximated by a layered half-space. A "layered half-space" refers herein to a multi-layered pavement with the lowest (bottom) layer assumed to extend to infinity. With this approximation, the profiles of each layer are assumed to be homogeneous and to extend to infinity in two horizontal directions. The layer profiles are assumed to be heterogenous in the vertical direction, often modeled by a number of layers with constant properties within each layer. In addition, it is assumed that the material in each layer is elastic and isotropic.

The operating principle of the SPA is based on generating and detecting stress waves in a layered medium. Five testing techniques are combined. Each test and its areas of strength are summarized in Table II.

TABLE II

| Strengths of Five Testing Techniques Used by Seismic Pavement Analyzer | |
|---|---|
| Testing Technique | Strengths |
| Ultrasonic Body Wave | *Young's Modulus of top layer of paving layer |
| Ultrasonic Surface Wave | *Shear modulus of top layer of paving layer |
| Impulse Response | *Shear modulus of subgrade; damping ratio |
| Spectral Analysis of Surface Waves | *Stiffness of each layer<br>*Thickness of each layer<br>*Variation in stiffness within each layer |
| Impact Echo | *Thickness of paving layer or depth to delaminated layer |

1. Seismic Body Waves

Wave motion created by a disturbance within an ideal whole-space can be described by two kinds of waves: compression waves and shear waves. Collectively, these waves are called body waves, as they travel within the body of the medium. Compression and shear waves can be distinguished by the direction of particle motion relative to the direction of wave propagation.

Compression waves (also called dilatational waves, primary waves, or P-waves) exhibit a push-pull motion. As a result, wave propagation and particle motion are in the same direction. Compression waves travel faster than the other types of waves, and therefore appear first in a direct travel-time record.

Shear waves (also called distortional waves, secondary waves, or S-waves) generate a shearing motion, causing particle motion to occur perpendicular to the direction of wave propagation. Shear waves can be polarized. If the directions of propagation and particle motion are contained in a vertical plane, the wave is "vertically polarized." This wave is called an SV-wave. However, if the direction of particle motion is perpendicular to a vertical plane containing the direction of propagation, the wave is "horizontally polarized." This wave is termed an SH-wave. Shear waves travel more slowly than P-waves and thus appear as the second major wave type in a direct travel-time record.

2. Seismic Surface Waves

In a half-space, other types of waves occur in addition to body waves. These waves are called surface waves. Many different types of surface waves have been identified and described. The two major types are Rayleigh waves and Love waves.

Surface waves propagate near the surface of the half-space. Rayleigh waves (R-waves) propagate at a speed of approximately 90 percent of S-waves. Particle motion associated with R-waves is composed of both vertical and horizontal components, that, when combined, form a retrograde ellipse close to the surface. However, with increasing depth, R-wave particle motion changes to a pure vertical and, finally, to a prograde ellipse. The amplitude of motion attenuates quite rapidly with depth. At a depth equal to about 1.5 times the wavelength, the vertical component of the amplitude is about 10 percent of that at the ground surface.

Particle motion associated with Love waves is confined to a horizontal plane and is perpendicular to the direction of wave propagation. This type of surface wave can exist only when low-velocity layers are underlain by higher velocity layers, because the waves are generated by total multiple reflections between the top and bottom surfaces of the low-velocity layer. As such, Love waves are not generated in pavement sections.

Body waves (shear and compression waves) and surface waves (Rayleigh waves) propagate away from a vertically vibrating circular source at the surface of a homogeneous, isotropic, elastic half-space. Approximately 67 percent of the input energy propagates in the form of R-waves. Shear and compression waves carry 26 and 7 percent of the energy, respectively. Compression and shear waves propagate radially outward from the source. R-waves propagate along a cylindrical wave front near the surface. Although body waves travel faster than surface waves, body waves attenuate in proportion to $1/r^2$, where r is the distance from the source. Surface wave amplitude decreases in proportion to $1/r^{0.5}$.

3. Seismic Wave Velocities

Seismic wave velocity is defined as the speed at which a wave advances in the medium. Wave velocity is a direct indication of the stiffness of the material; higher wave velocities are associated with higher stiffness. By employing elastic theory, compression wave velocity can be defined as:

$$V_p = \left[ \frac{\lambda + 2G}{\rho} \right]^{0.5} \tag{1}$$

where $V_p$=compression wave velocity, $\lambda$=Lame's constant,

G=shear modulus, and $\rho$=mass density.

Shear wave velocity, $V_s$, is equal to:

$$V_s = \left( \frac{G}{\rho} \right)^{0.5} \tag{2}$$

Compression and shear wave velocities are theoretically interrelated by Poisson's ratio:

$$\frac{V_p}{V_s} = \left[ \frac{(1-v)}{(0.5-v)} \right]^{0.5} \tag{3}$$

where $v$ is the Poisson's ratio. For a constant shear wave velocity, compression wave velocity increases with an increase in Poisson's ratio. For a $v$ of 0.0, the ratio of $V_p$ to $V_s$ is equal to °2; for a $v$ of 0.5 (an incompressible material), this ratio is infinity.

For a layer with constant properties, R-wave velocity and shear wave velocity are also related by Poisson's ratio. Although, the ratio of R-wave to S-wave velocities increases as Poisson's ratio increases, the change in this ratio is not significant. For Poisson's ratio of 0.0 and 0.5, this ratio changes from approximately 0.86 to 0.95, respectively. Therefore, it can be assumed that the ratio is equal to 0.90 without introducing an error larger than about 5 percent. Equation 3 can be rewritten as:

$$v = \frac{\left[ 0.5 \left( \frac{V_p}{V_s} \right)^2 - 1 \right]}{\left[ \left( \frac{V_p}{V_s} \right)^2 - 1 \right]} \tag{4}$$

Equation 4 can then be used to calculate Poisson's ratio $v$ once $V_s$ and $V_p$ are known.

4. Elastic Constants

Propagation velocities per se have limited use in engineering applications. In pavement engineering, Young's modulus (E) of each of the different layers should be measured. Therefore, calculating the elastic moduli (Young's modulus (E) and shear modulus (G)) from propagation velocities is important.

Shear wave velocity, $V_s$, is used to calculate the shear modulus, G, by $$G = \rho V_s^2 \tag{5}$$

in which $\rho$ is the mass density. Mass density is equal to $Y_t/g$, where $Y_t$ is the total unit weight of the material, and g is gravitational acceleration. If Poisson's ratio $v$ (or compression wave velocity) is known, other moduli can be calculated for a given $V_s$. Young's modulus (E) and shear modulus (G) are related by:

$$E = 2G(1+v) \tag{6}$$

or $$E = 2\rho V_s^2 (1+v) \tag{7}$$

In a medium where the material is restricted from deformation in two lateral directions, the ratio of axial stress to axial strain is called constrained modulus. Constrained modulus, M, is defined as:

$$M = \rho V_p^2 \tag{8}$$

or in terms of Young's modulus E and Poisson's ratio $v$:

$$M = \frac{(1-v)E}{(1+v)(1-2v)} \tag{9}$$

The Bulk modulus, B, is the ratio of hydrostatic stress to volumetric strain and can be determined by:

$$B = M - \frac{4}{3} G \tag{10}$$

B. Measurement Procedure

Diagnosis of distress precursors according to the present invention is based on measuring mechanical properties and thicknesses of each of the pavement system layers using propagation of seismic waves. Typical cross-sections of a flexible pavement and a rigid pavement are shown in FIGS. 17 and 17A. As shown in FIG. 17, a flexible paving layer 10 typically consists of an upper layer made of asphaltic concrete 11 with a typical thickness, h1, of 25 mm to 200 mm. Underlying this layer is a base course 12 with a typical thickness, h2, of 100 mm to 300 mm, and comprising densely packed granular material such as sand, rocks, etc. The final, bottom-most layer, is denoted the subgrade layer 13, and comprises the original soil. An optional subbase 14 course comprising densely packed granular material of 100 mm to 300 mm thickness may be placed between the base 12 and the subgrade 13.

Typical rigid paving layers 15 are illustrated in FIG. 17A, and contain two to three layers. The top layer 17 is typically comprised of Portland cement concrete with a typical thickness, h4, of 150 mm to 300 mm. Under the top layer 17 is the subgrade 18, which typically comprises the original soil. An optional base course 19 may be placed between the concrete layer 17 and the subgrade 18, with a thickness h5 typically ranging between 100 mm to 300 mm and comprises of densely packed granular material.

The SPA lowers transducers (receivers) and sources to the top layer of the pavement, be it asphaltic concrete or Portland cement concrete (or some other suitable top paving layer) and digitally records surface deformations induced by a large pneumatic hammer which generates low-frequency vibrations (i.e., in a frequency range of about 0–1200 Hz), and a small pneumatic hammer which generates high-frequency vibrations (i.e., in a frequency range of about 100–50 kHz) (see FIG. 1).

This transducer frame is preferably mounted on a trailer that can be towed behind a vehicle and is similar in size and concept to a Falling Weight Deflectometer (FWD). However, the SPA differs significantly from the FWD in that more and higher frequency transducers are used, and more sophisticated interpretation techniques are applied. Further, the FWD was never intended to be used to locate fine cracks, overlay delamination or moisture in pavement layers or to quantify aging in asphalt. The SPA can be used for these distresses because it uses much higher frequency levels in the load than the FWD. This is not to say, however, that the SPA is meant to replace the FWD. Rather, the SPA may be used with the FWD, as pavements behave much differently under the FWD than the SPA.

The SPA preferably comprises menu-driven software that may be controlled by an operator at a computer connected to the trailer by a cable. The computer may be run from the cab of the truck towing the SPA or from various locations around the SPA. In addition, the computer may be operated remotely over a telephone line via a modem.

The pavement measurements are preferably spot measurements; that is, the device is towed and situated at a specific point before measurements are be made. A complete testing cycle, which includes situating at the site, lowering the sources and receivers, making measurements, and withdrawing the equipment, generally takes less than one minute according to the present invention. During this one minute, most of the data reduction is also executed.

For rigid pavements (see FIG. 17A), the SPA measures the stiffness and Poisson's ratio of the concrete layer 17, the stiffness of material under the concrete (base course) 18, and the damping of the slab. A slab is a portion of the concrete layer between spacing elements. The concrete layer will thus comprise several individual slabs coupled by spacing elements, which are placed to allow for expansion and contraction of the rigid concrete layer. For flexible pavements (see FIG. 17), the SPA measures the stiffness and effective thickness of the asphaltic-concrete surface layer 11, the stiffness/thickness of the base 12, and the stiffness of the subgrade 13. For both types of pavements, the SPA also preferably records the ambient and pavement surface temperatures and the distance from a given point.

The appropriate spacing of measurements depends on the intended use. For maintenance, a procedure similar to that of the FWD can be used. However, for high-precision diagnostics, tests should be carried out every 0.3 m to 30 m, depending on the expected nature of distress. The lower limit of 0.3m spacing is suitable for precision mapping of delaminated areas or loss of support under Portland cement concrete. The upper limit of 30m is suitable for determining the general variation in the condition of pavement. For rigid pavements, test spacing depends on the joint spacing. Typically the two joints and at least the middle of the slab should be tested. For research purposes, the frequency of measurement should be based on the goals of the research.

An extensive field study has determined the effects of temperature on the results of different tests. This study concluded that testing rigid pavements at ambient temperatures in excess of 35° C. is not feasible. For flexible pavements, the temperature should not exceed 50° C. At such high temperatures, the asphalt concrete layer is too viscous and coupling of energy to it is difficult. To minimize the effects of fluctuation in the moisture level due to precipitation, the equipment should not be used until one day after significant precipitation. As described above, the short-term transient change in moisture is not of any practical interest in maintenance activities.

C. Data Analysis

The SPA according to the present invention collects three levels of data. The first level is raw data. These are the waveforms generated by hammer impacts and collected by the transducers. The second level is processed data. These are pavement-layer properties derived from the raw data through established theoretical models. The third level is interpreted data. These are diagnoses of pavement distress precursors from data processed through models. Processed data may be archived with the interpretations so that the user or manufacturer can test and upgrade the interpretation models.

The raw data (waveforms) collected from the hammer impacts may be processed immediately and saved for archival only if specifically requested. Each of eight vibration sensors records three impacts. The storage requirements for saving these raw data are large (up to 0.4 megabytes per sample). If desired, the SPA can save these data for troubleshooting or research on enhanced processing techniques.

Processed data are the result of calculations performed on the raw data and are independent estimates of the physical properties of the pavement system. These calculated properties may be archived for all measurements. Table III lists the pavement properties estimated from the raw data. Young's modulus is estimated from compressional velocity measurements in the asphaltic concrete or Portland cement top layer and from mechanical impedance in the base (Ultrasonic Body Wave test). The shear modulus is estimated from surface wave velocity dispersion (Ultrasonic Surface Wave test). Thicknesses are estimated with the impact echo in the concrete layer and with Spectral Analysis of Surface Waves and Impact Echo tests conducted in the asphaltic concrete and base layers. Damping is estimated from the Impulse-Response method.

TABLE III

Pavement Properties Estimated by the Seismic Pavement Analyzer

| Pavement Component | Parameter Measured | | | | |
|---|---|---|---|---|---|
| | Young's Modulus | Shear Modulus | Thickness | Damping | Other |
| Top Paving Layer | yes | yes | yes | no | Temperature |
| Base | yes | yes | yes* | no | |
| Subgrade | no | yes | no | yes | |

*Thickness estimate of base depends on shear modulus contrast with subgrade.

Interpreted data are diagnoses of distress precursors. Table IV lists the seven distress types to be diagnosed from the physical property measurements listed in Table III. The "Candidate for Rehabilitation" category is included in the pavement and base layers for conditions where failure appears to be imminent and maintenance or rehabilitation should have already occurred.

TABLE IV

Distress Precursor Interpretations
from Pavement Properties

Paving Layer Distress Precursors

Fine cracking
Aging
Delamination
Candidate for rehabilitation

Base Distress Precursors

Void under pavement
Softening of base under pavement
Moisture change in base
Candidate for rehabilitation D. Data Interpretation The interpretation technique assumes that the distress precursors to be identified are specific to a given pavement layer or are essentially independent of the presence of other distress precursors. Aging, fine cracking, overlay delamination, and voids are directly observable physical conditions unrelated to a failure model. Moisture in the base and under joints is strongly related to a failure model, but infiltration paths may be highly localized and not seen in the measurements.

Presuming independence of the distress precursors permits a layer-by-layer diagnosis, since the SPA measurements (Table III) are also layer specific. Aging of asphalt is diagnosed through an increase in brittleness, apparent in Young's and shear moduli; delamination is apparent in thickness and echo size. Fine cracking in pavement is diagnosed through a strong reduction in the shear modulus, relative to a reduction in Young's modulus. In the base, voids and moisture both reduce stiffness, while voids present a relatively undamped system compared to the presence of moisture.

According to the present invention, distress precursors are interpreted with a hypothesis-testing approach, relative to the design parameters for the pavement system. In general, the diagnosis involves the following. Data to be diagnosed is normalized by default values based on design parameters of the pavement. Each major distress type that may be detected by the device of the present invention has a set of associated relative-value polygons. Each polygon is derived from extreme values of parameters associated with the particular distress type. The measured values associated with the particular distress type are compared against the polygon to determine a relative value within the polygon, or within the extreme ranges. For instance, if fine cracking exists, then Young's and shear moduli in the pavement will fall within a specified range of values that are a fraction of the ideal stiffness for the concrete type used. These ranges are predetermined based on knowledge in the field. For example, a high damping and high stiffness measurement for a base will indicate that the measured is "good," as it is known in the field that a base with a high damping factor and a high stiffness is deemed to be "good." If measurement points fall outside these ranges for known distress types, distances from the measurement points to the region will be used to weight the probability that the hypothesis is true.

The diagnosis procedure may be a routine run optionally at the end of a data collection set-up, or on large sets of data, as defined in a list of data points for which diagnosis is desired. The device of the present invention will preferably inform the user verbally or graphically of the evaluation of the paving layers with respect to the distress precursors under examination. Thus, in the preceding example, the device would return a suitable message to the user, such as "Base good."

E. Principles of Measurements

The Table below contains a summary of the measurement techniques and theories for the different distress precursors that are investigated by the device and method of the present invention.

TABLE V

Levels and Nature of Measurements for Each Distress Precursor

| Distress Precursor | Test | Quantity Measured | Pavement Component Evaluated |
|---|---|---|---|
| Moisture in Base | Impulse Response | Change in flexibility due to change in moisture content | Overall pavement system (single value for all layers combined) |
| | Spectral Analysis of Surface Waves (SASW) | Change in Young's modulus due to change in moisture content | Base, subbase and subgrade |
| Fine Cracking | Impulse Response | Reduction in rigidity of the paving layer due to cracks | Overall pavement system |
| | Ultrasonic Body Wave Velocity | Delay in travel time of compressional wave because of longer travel path and lower rigidity | Upper layer |
| Voids or Loss of Support | Impulse Response | Significant increase in | Supporting layer |

TABLE V-continued

Levels and Nature of Measurements for Each Distress Precursor

| Distress Precursor | Test | Quantity Measured | Pavement Component Evaluated |
|---|---|---|---|
| | | flexibility of slab due to lack of support under the slab | (subgrade) |
| | Impact Echo | Return (resonant frequency) associated with the thickness of slab | Upper layer (asphalt or concrete) |
| Overlay Delamination | Impulse Response | Significant increase in flexibility of overlay due to lack of support under the overlay | Overall pavement system |
| | Impact Echo | Return (resonant) frequency associated with the thickness of overlay | Overlay (layer on top of paving layer) |
| Aging (flexible pavements only) | Ultrasonic Surface Waves | Shear wave velocity of asphaltic-concrete layer | Asphaltic-concrete layer |
| | Ultrasonic Body Wave Velocity | Poisson's ratio, by measuring compression wave velocity of Asphaltic-concrete layer and combining with shear wave velocity | Asphaltic-concrete layer |

1. Moisture in Base

The Impulse-Response method presumes that the paving material becomes less rigid (more flexible) as its water content increases. This is true for most paving materials, except concrete and some stabilized foundation layers. High flexibility of these materials indicates the need for maintenance.

Similarly, as the water content increases in the foundation layers, the materials become less stiff. By measuring the shear wave velocity profile of a given site using the Spectral Analysis of Surface Waves (SASW) method, one can determine the location and the amount of decrease in moduli of different layers in the pavement.

2. Fine Cracking

The Impulse-Response method presumes that a cracked section of pavement is less rigid than an intact one. The limitation of this method is that the crack has to propagate through the thickness of the paving layer.

The Ultrasonic-Body-Wave method can determine the existence of cracks, even if they have not extended through the thickness of the layer. In this method, seismic wave energy is generated at one point and detected at several other points. Any cracks in the material located between the source and the receiver will delay the direct propagation of waves and will reduce the amplitude associated with the arriving wave.

3. Voids or Loss of Support

A void beneath or within a slab results in increased flexibility of the slab. Therefore, measuring the flexibility of the slab at different locations using the Impulse-Response method can pinpoint the voids or loss of support.

The Impact-Echo method distinguishes between overlay delamination and voids beneath or within the slab. (This method assumes that the Ultrasonic-Body-Wave method has already computed the Young's modulus), can also determine the depth to the reflector. The reflector is the delamination, if present; otherwise, it is the bottom of the slab.

4. Overlay Delamination

The Impulse Response and the Impact Echo are the prime methods for determining the location and existence of delamination. The theoretical and experimental aspects of using these two tests for detecting overlay delamination are identical to those used for locating voids and loss of support. The only differences are the nature and location of the interface. For delamination, the void occurs at the interface of two layers and the delaminated layer is located closer to surface.

5. Pavement Aging

An aging asphalt layer becomes stiffer and more brittle. By measuring compression wave velocity and Poisson's ratio, one can determine the effect of aging on the behavior of the asphalt layer. The shear modulus increases and Poisson's ratio decreases as the layer ages. The Ultrasonic-Surface-Waves method (described hereinafter) can determine the shear wave velocity of the asphalt layer. Direct compression wave propagation using the Ultrasonic-Body-Waves method can determine the compression wave velocity. Knowing the shear and compression wave velocities, one can determine Poisson's ratio of the material, which is used to evaluate the existence of fine cracking in a pavement layer.

F. Description of Measurement Technologies

1. Impulse-Response (IR) Method

Two parameters are obtained with the IR method—the shear modulus of subgrade and the damping ratio of the system. These two parameters characterize the existence of several distress precursors. In general, the stiffness of subgrade can be used to delineate between good and poor support. The damping ratio can distinguish between the loss of support or weak support. The two parameters are extracted from the flexibility spectrum measured in the field. An extensive theoretical and field study shows that except for thin layers (less than 75 mm) and soft paving layers (i.e., flexible pavements), the stiffness obtained by the IR method is a good representation of the shear modulus of subgrade, and the stiffness of the paving layers would influence the results insignificantly. See Reddy, S., "Determination of Voids in Rigid Pavements Using the Impulse Response Method," *M.S. Thesis, The University of Texas at El Paso, El Paso* (1992), the disclosure of which is herein incorporated by reference. In other cases, the properties of the pavement layers (asphaltic-concrete and base) affect the outcome in such a manner that the stiffness obtained from the IR test should be considered as an overall modulus.

The IR tests use a low-frequency seismic source and a geophone. The pavement is impacted to couple stress wave energy in the surface layer. The geophone measures the particle velocity through the paving layer by transforming seismic energy imparted to the pavement into an electrical voltage proportional to the velocity of the seismic wave motion. Exemplary geophones 41 are model L28-LBH geophones manufactured by Mark Products. At the interface of the surface layer and the base layer, a portion of the seismic energy is transmitted to the bottom layers, and the remainder is reflected back into the surface layer. The force of the hammer impact is measured with a load cell within the hammer head of the low-frequency source. The load cell outputs an electrical voltage proportional to the weight or force that is acting upon it. The response of the pavement, in terms of seismic wave velocity, is monitored with the geophone and then numerically converted to displacement. The load and displacement time-histories are simultaneously recorded and are transformed to the frequency domain using a known Fast-Fourier Transform algorithm. The ratio of the displacement and load (termed flexibility) at each frequency is then determined.

For analysis purposes, the pavement is modeled as a single-degree-of-freedom (SDOF) system. Three parameters are required to describe such a system: natural frequency, damping ratio, and gain factor. The last two can be replaced by the static amplitude and the peak amplitude. These three parameters are collectively called the "modal parameters" of the system. The natural frequency and gain factor are used to determine the stiffness of subgrade. The damping ratio is used directly.

To determine the modal parameters, a curve is fitted to the flexibility spectrum according to an elaborate curve-fitting method that uses the coherence function as a weighting function. See Richardson, M. H., and D. L. Formenti, "Parameter Estimation from Frequency Response Measurements Using Rational Fraction Polynomials," *Proceedings, First International Modal Analysis Conference* (Society for Experimental Mechanics, Orlando, Fla.), pp. 167-81 (1982), the disclosure of which is herein incorporated by reference. The standard form of the equation fitted to data is:

$$A_s(\omega) = B \frac{\sum_{i=1}^{n}(S - Z_i)}{\sum_{i=1}^{n}(S - P_i)} \quad (11)$$

where:

$A_s(\omega)$=flexibility at a frequency f,

S=Laplace operator=$j(2\pi f)$, $Z_i$=ith zero, $P_i$=ith pole, n,m=number of poles and zeros, and B=gain factor.

The poles, zeros, and gain factor obtained from the curve-fitting are easily converted to modal parameters. From these parameters, the stiffness of subgrade is determined. The shear modulus of subgrade, G, is calculated from the following relationship, as discussed in Dobry, R., and G. Gazetas, "Dynamic Response of Arbitrary Shaped Foundations," *Journal of Geotechnical Engineering* (American Society of Civil Engineers, New York), vol. 2, pp. 109–35 (1986):

$$G = \frac{(1-v)}{(2 L A_o I_s S_z)} \quad (12)$$

where v=Poisson's ratio of subgrade

L=length of slab, and $A_o$=static flexibility of slab (flexibility at f=0).

The shape factor, $S_z$, has also been developed by Dobry and Gazetas. The value of $S_z$ is equal to 0.80 for a long flexible pavement.

$I_s$ is a parameter that considers the effect of an increase in flexibility near the edges and corners of a slab. The parameter $I_s$ is a function of the length and width of the slab, as well as the coordinates of the impact point relative to one corner. Depending on the size of the slab and the point of impact, the value of $I_s$ may be as high as 6.

The damping ratio, which typically varies between 0 to 100 percent, is an indicator of the degree of the slab's resistance to movement. A slab that is in contact with the subgrade or contains a water-saturated void demonstrates a highly damped behavior and has a damping ratio of greater than 70 percent. A slab containing an edge void would demonstrate a damping ratio in the order of 10 to 40 percent. A loss of support located in the middle of the slab will have a damping of 30 to 60 percent.

2. Spectral-Analysis-of-Surface-Waves (SASW) Method

The development of the Spectral-Analysis-of-Surface-Waves (SASW) method is detailed in Nazarian, S., and K. H. Stokoe, "Nondestructive Evaluation of Pavements by Surface Wave Method," *STP 1026, American Society for Testing and Materials, Philadelphia, Pa.*, (1989), the disclosure of which is herein incorporated by reference. SASW is a seismic method that may determine shear modulus profiles of pavement sections nondestructively.

A key point in the SASW method is the measurement of the dispersive nature of surface waves. A complete investigation of a site with the SASW method consists of collecting data, determining the experimental dispersion curve, and determining the stiffness profile (inversion process).

An exemplary configuration for the SPA is depicted in FIG. 1. For the SASW tests, all accelerometers 42 and geophones 41 are active in three separate banks, with a first bank comprising the near accelerometers and the high-frequency source, a second bank comprising the far accelerometers and the high-frequency source, and a third bank comprising the geophones and the low-frequency source. As used herein, "near accelerometers" will refer to accelerometers 42a, 42b, 42c, and "far accelerometers" will refer to accelerometers 42c, 42d, 42e (FIG. 1). The transfer function and coherence function between pairs of receivers are determined during the data collection. The phase information of the cross-power spectra and the coherence functions from several receiver spacings are used to determine a representative dispersion curve in an automated fashion. The last step is to determine the elastic modulus of different layers, given the dispersion curve.

The accelerometers are transducers whose output is proportional to particle acceleration through the paving layer in response to the impact of a seismic source. Exemplary accelerometers 42 are model 308B02 accelerometers manufactured by PCB Piezoelectronics, Inc.

3. Ultrasonic-Surface-Wave Method

The Ultrasonic-Surface-Wave method is an offshoot of the SASW method. The major distinction between these two methods is that in the Ultrasonic-Surface-Wave method, the properties of the top layer of the paving layer may be easily and directly determined without a complex inversion technique. "Ultrasonic," when used herein, refers to frequencies greater than about 20 kHz. To implement the method, a high-frequency source and accelerometers are utilized.

The theory of computation is essentially as follows. Up to a wavelength approximately equal to the thickness of the uppermost layer, the velocity of propagation is independent of wavelength. Therefore, if one simply generates high-frequency (short-wavelength) waves, and if one assumes that the properties of the uppermost layer are uniform, the shear modulus of the top layer, G, may be determined from $$G = \rho[(1.13-0.16)\nu \, V_{ph}]^2 \quad (13)$$

where $V_{ph}$ = velocity of surface waves $\rho$ = mass density $\nu$ = Poisson's ratio.

The thickness of the surface layer may be estimated by determining the wavelength above which the surface wave velocity is constant.

This methodology may be simplified even further. If one assumes that the properties of the uppermost layer are uniform, the shear modulus of the top layer, G, may be determined from $$G = \rho \left[ (1.13 - 0.16\nu) \left( \frac{m}{360D} \right) \right]^2 \quad (14)$$

Parameter m (deg/Hz) is the least-squares fit slope of the phase of the transfer function in the high-frequency range. D refers to the distance between the two receivers.

4. Ultrasonic Body Wave Velocity Measurement

Once the body wave velocity of a material is known, its Young's modulus may be readily determined. The same set-up used to perform the SASW tests may be used to measure body (compression) wave velocity of the upper layer of pavement.

It has been found that when the surface of a medium is impacted, the generated stress waves propagate mostly with Rayleigh wave energy and, to a lesser extent, with shear and compression wave energy. As such, the body wave energy present in a seismic record generated using the set-up shown in FIG. 1 is very small; for all practical purposes it does not contaminate the SASW results. However, compression waves travel faster that any other type of seismic wave, and are detected first on seismic records.

In a preferred method according to the present invention, times of first arrival of compression waves are measured by triggering on an amplitude range within a time window.

5. Impact-Echo Method

The Impact-Echo method may effectively locate defects, voids, cracks, and zones of deterioration within concrete. The method has been thoroughly studied and effectively used on many projects by researchers at the National Institute of Standards and Technology.

For this test, a high-frequency source and at least one accelerometer are used. Once the compression wave velocity of concrete, $V_p$, is known, the depth-to-reflector, T, may be determined from:

$$T = \frac{V_p}{2f} \quad (15)$$

where f is the resonant (return) frequency obtained by transforming the deformation record into the frequency domain.

Thus, a seismic pavement analyzer has been disclosed that may accurately and automatically identify several types of distress precursors that contribute to pavement deterioration. The SPA may be used not only to identify pavement distress at an early stage, but it may also be used to verify the effectiveness of preventive treatments.

The advantages of the present invention will be further appreciated from the drawings and from the detailed description provided below.

BRIEF DESCRIPTION OF THE DRAWINGS

The herein described advantages and features of the present invention, as well as others which will become apparent, are attained and may be understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

FIG. 2 is a top-view diagram of major mechanical components of a seismic pavement analyzer according to the present invention.

FIG. 2A is a side-view diagram of major mechanical components for a seismic pavement analyzer according to the present invention.

DETAILED DESCRIPTION

The Seismic Pavement Analyzer (SPA) according to the present invention consists of two hardware subsystems, and three software subsystems. The first hardware subsystem consists of the mechanical components, including the transducers, sources, and their mountings; the second hardware subsystem consists of the electronic components, including signal conditioning, data acquisition, and controls. The three software subsystems are data acquisition, data interpretation, and database management. These components are described below.

A. Hardware Subsystems

1. Mechanical Components

Figure 1:
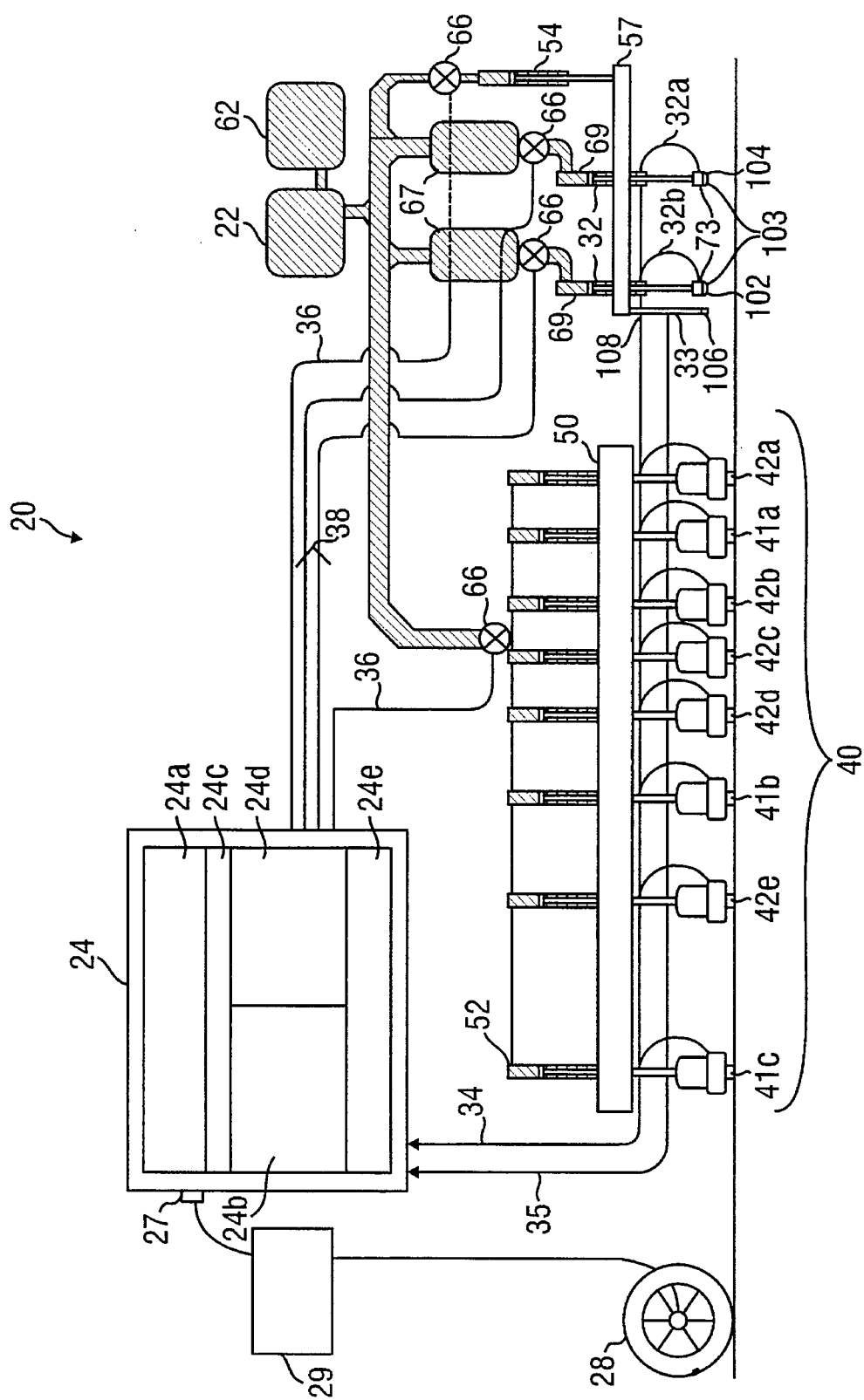
FIG. 1 is a schematic diagram of a seismic pavement analyzer according to the present invention.

An exemplary configuration for SPA 20 is shown in FIGS. 1 and 2. As shown in FIG. 1, SPA 20 preferably includes hammers (sources) 32, transducers (receivers) 40, transducer mounting member 50, pneumatic cylinders 52 to raise and lower transducers 40, and computer 24. Control lines 38 from computer 24 control the operation of sources 32, and control lines 36 control the raising and lowering of transducers 40. Control line 34 gathers electrical signals from transducers 40 and sources 32 and feeds the information back to computer 24. Temperature sensor 33 includes pavement temperature sensor 106 and air temperature sensor 108, and gathers temperature information to feed back to computer 24 over electrical line 35.

Computer 24 includes personal computer (PC) 24a, analog-to-digital (A/D) converter board 24b, PC bus 24c, input/output (I/O) board 24d, as well as conditioning and control circuitry 24e. Conditioning and control circuitry 24e includes programmable gain circuit 84, accelerometer and load cell conditioning 86, analog multiplexer 88, geophone conditioning 90, temperature conditioner 112, control line buffering 114 and source fire control 116. (See FIGS. 4, 6, and 6A).

Transducers 40 may comprise, for example, three geophones 41 and five accelerometers 42. As used herein, "near accelerometers" will refer to accelerometers 42a, 42b, 42c, and "far accelerometers" will refer to accelerometers 42c, 42d, 42e. Sources 32 comprise low-frequency pneumatic hammer 32a and high-frequency pneumatic hammer 32b. Other configurations of transducers 40 and sources 32 will be apparent to those of skill in the art. Low-frequency source 32a further comprises low-frequency load cell 104 within hammer head 73, and high-frequency source 32b further comprises high-frequency load cell 102. Load cells 102 and 104 measure the impact of the force of sources 32. An exemplary load cell is the model 221A05, manufactured by PCB Piezoelectronics, Inc.

Distance wheel 28 measures the distance traveled by SPA 20, and sends a distance signal to distance measurement electronics 29, which may be, for example, an AMU™ 2000 meter. Distance measurement device 29 inputs a distance measurement to computer 24 through serial port 27.

Figure 5:
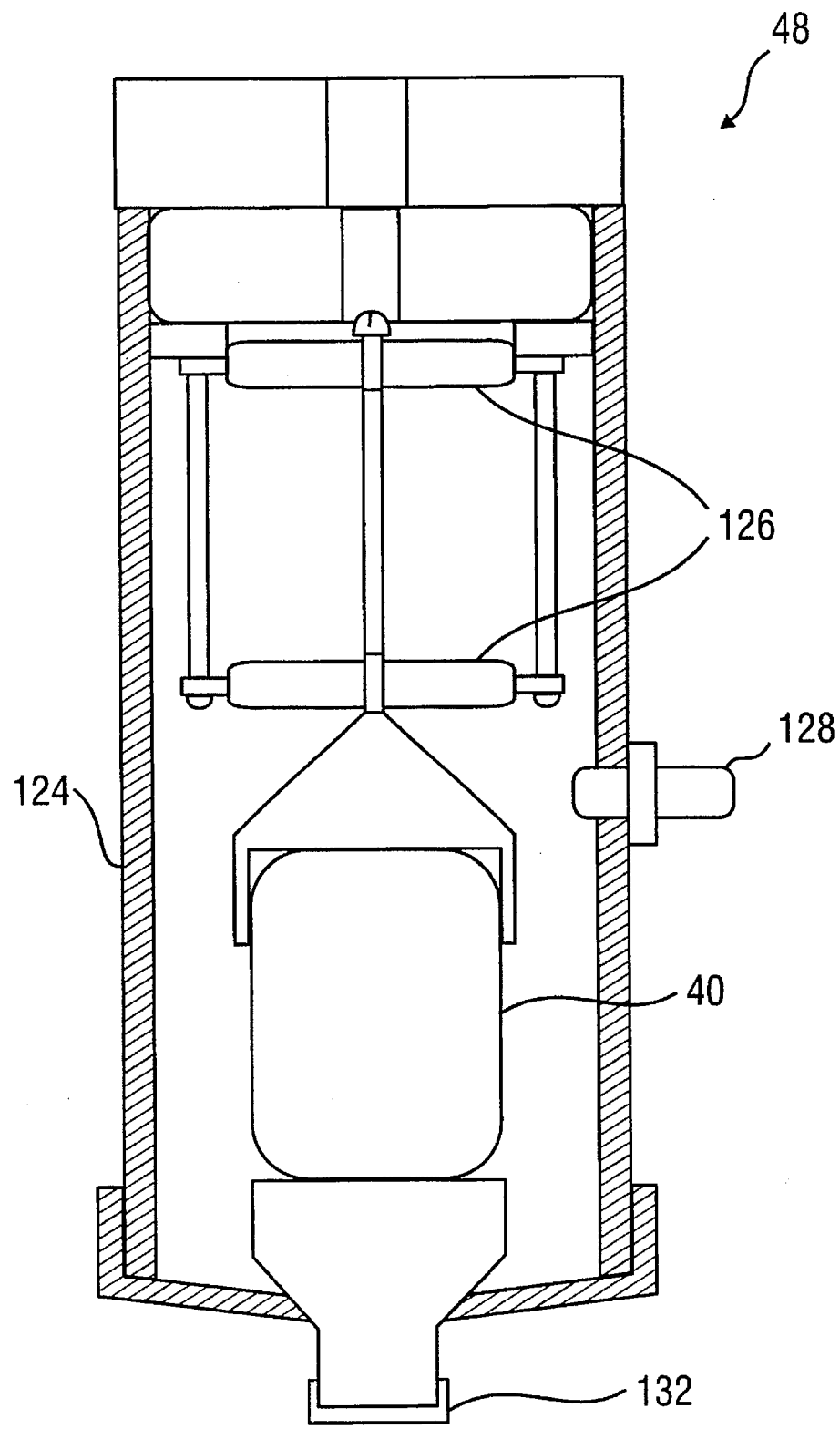
FIG. 5 is a diagram of a geophone and accelerometer mounting according to the present invention.

The major mechanical components of the Seismic Pavement Analyzer (SPA) are schematically depicted in FIG. 2. These include transducer mounting bar 50 holding the geophone and accelerometer pneumatic cylinders 52. Transducers 40 (not shown in FIG. 2) are housed within individual transducer holders 48 (FIG. 5). SPA 20 also includes two pneumatic hammer sources 32 that are raised and lowered to the pavement surface. These components may be mounted on two-wheel trailer 26 for towing behind a car or truck. Box 46 at the rear of trailer 26 may hold a pressurized air supply, pneumatic and electronic controls (valves, regulators), a moisture trap to minimize the moisture in the pneumatic system, and electronics to isolate the computer from the control valves.

Figure 3:
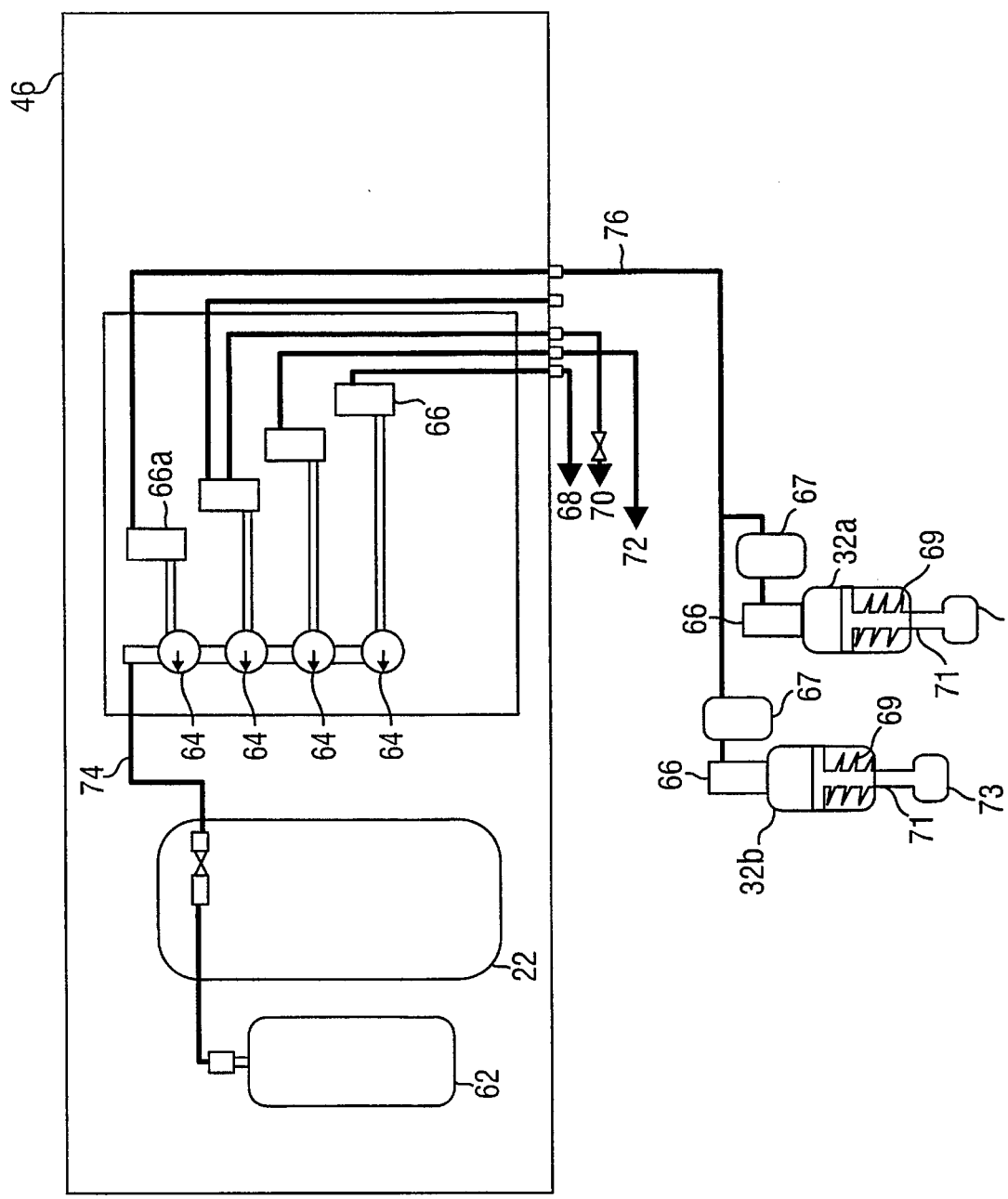
FIG. 3 is a diagram of an air-control system for a seismic pavement analyzer according to the present invention.

A schematic of the air control system housed in box 46 is shown in FIG. 3. The air control system includes compressor 62, air tank 22, regulators 64, and electrical solenoid valves 66.

Figure 4:
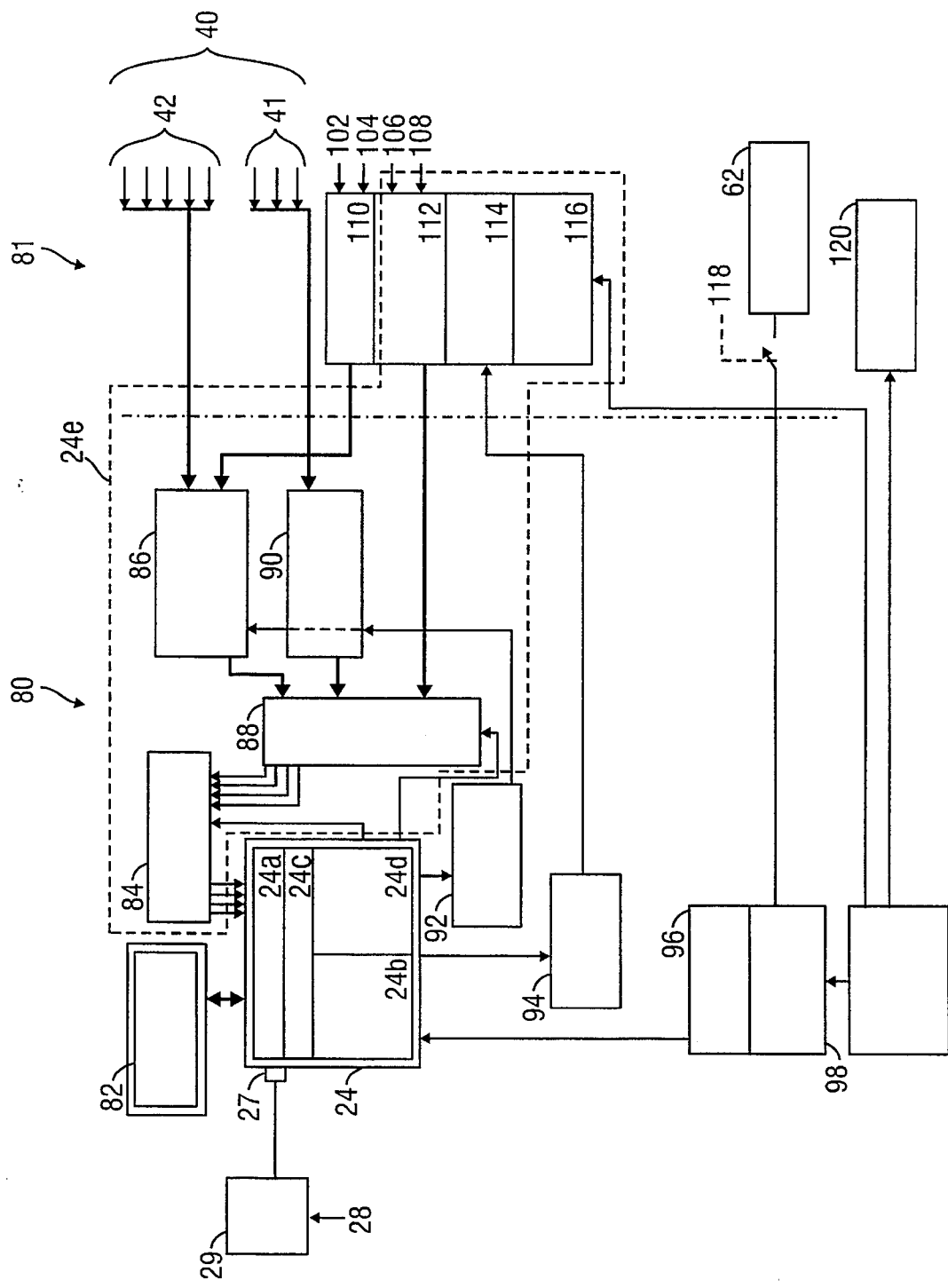
FIG. 4 is a block diagram of major electric components for a seismic pavement analyzer according to the present invention.

The major electrical components of the Seismic Pavement Analyzer are schematically shown in FIG. 4. These include power supply 100, computer 24 for data acquisition and analysis, signal conditioning electronics 86, 90, 112, and control electronics 94, 114, 116.

The individual elements of each of these three systems are described in greater detail below.

a. Transducer Mounting

As shown in FIG. 2, transducer mounting 50 preferably consists of a 17-mm channel, mounted to the body of trailer 26 with pneumatic springs 56. Springs 56 isolate transducer mounting 50 from trailer 26 and source vibrations and also allow several centimeters of vertical adjustment for pavement topography. Individual spring-return air cylinders 52 raise and lower the transducers 40 (FIG. 1) to the pavement. With this design, significant pavement topography is accommodated with a uniform transducer coupling force, and less noise is coupled from the trailer to the transducers.

Geophone and accelerometer transducer holders 48, as shown in FIG. 5, protect transducers 40 from the elements and isolate the transducers from vibrations of mounting bar 50. This design has proved to have excellent coupling and high-frequency response. Shell 124 of holder 48 is constructed of PVC pipe, which shows very little resonance and prevents steel-aluminum contact that could cause corrosion. Rubber vibration isolators 126 connecting transducers 40 to the raise/lower mechanism 52 (FIGS. 1, 2) have given reliable coupling on even the rougher chip-seal surfaces.

As shown in FIGS. 1 and 3, two air cylinders 69 lower the high-frequency and low-frequency pneumatic sources, 32*b* and 32*a*, respectively, on their mounting assembly 57 (FIG. 2A) to rest on the pavement surface. Pneumatic hammers 73 in sources 32 preferably give good high-frequency and low-frequency signals of adequate strength that are very repeatable. Accumulator 67, with a computer-controlled solenoid valve 66, preferably has an adequate cycle time of less than 0.5 second. The source feedback control circuit adjusts the fire time based on the signal shape.

Air cylinders 69 and raise/lower mechanism 52 may each comprise the same type of mechanism, such as a Bimba model D-48179-A-12.

The transducer-mounting member 50 of SPA 20 may be a 50 mm by 150 mm U-channel that is about 180 cm long. Individual geophone and accelerometer air cylinders 52 are bolted to this U-channel, transducer holders 48 are mounted to air cylinders 52, and the necessary electrical cables are preferably routed underneath the U-channel.

Transducer-mounting member 50 is preferably mounted to trailer 26 through four manually controlled air springs 56 (FIG. 2) that provide vibration isolation with some height and level adjustment to accommodate different tow-vehicle heights. The weight of each transducer 40 (FIG. 1) is counterbalanced by a spring in its air cylinder 52. Air cylinders 52 preferably have a useful throw of at least 40 cm and, fully retracted, transducers 40 preferably have a clearance of about 20 cm for high-speed travel. This clearance provides durability of the raise/lower mechanism through numerous bendings and straightenings.

It is preferred that positive air pressure be required to lower transducers 40 so that in the event of electrical or pneumatic failure, transducers 40 rise so that trailer 26 may be safely towed for repair. The individually mounted, spring-return air cylinders 52 accommodate a wide range of pavement or pothole topography with a uniform force coupling the transducer to the pavement.

b. Geophone and Accelerometer Mounting

The transducer holder 48 for transducers 40 is shown in FIG. 5. Holder 48 preferably comprises 50-mm-diameter polyvinyl chloride (PVC) tube 124 that provides a nonresonant protection and centering support. Transducers 40 are isolated from air cylinders 52 with rubber vibration isolators 126. Thin rubber feet 132 may be used on the transducers to provide a relatively uniform, damped coupling with various pavement surfaces. A gland 128 may be provided in a wall of tube 124 for connection to necessary controlling wires. Holders 4*e* may be screwed onto the control air cylinder 52 (FIG. 1) and tightened with lock nuts.

c. Source Mounting

As shown in FIG. 2, high- and low-frequency pneumatic hammers 32 may be mounted to movable frame 57 that is attached through air cylinder 54 to trailer axle 55. Air pressure may be used to lower source frame 57 to the pavement surface to help ensure uniform source height from sample to sample. Hammers 32 may be raised by springs and air pressure to help ensure adequate clearance during travel. Further, hammers 32 may be isolated from transducer-mounting member 50 by both the lowering air cylinders 52 and transducer-mounting-member air springs 56. The mounting permits adjustment of the stroke of hammer 32 that may be required to control hammer force in extreme variations of pavement conditions. Hammer heads 73 (FIGS. 1, 3) in the high- and low-frequency sources 32 preferably comprise load cells (102, 104) to measure the applied force of the hammer hits. The load cells measure force in both extension and compression.

d. Pneumatic Control

The general schematic design of the pneumatic control system is shown in FIG. 3. Air pressure is preferred in the SPA to raise and lower the transducers 40 and to impact the low- and high-frequency hammers 32. A 120-volt (or 12-v) compressor 62 may be used to charge air tank 22 that provides air power during operation through inflow line 74 into regulators 64. Air pressure is provided through line 68 to lower sources 32, through line 70 to raise sources 32, and through line 72 to operate the transducer air cylinders. Air compressor 62 may be controlled by pressure switch 118 (see FIG. 4) that preferably turns on at 40 psi (280 kPa) and turns off at 60 psi (420 kPa). Exemplary individual circuit pressures are about 40 psi (280 kPa) for firing sources 32 (line 76), 20 psi (140 kPa) for raising and lowering hammer assembly 54 (lines 70 and 68), and 15 psi (105 kPa) for holding down transducer 40 (line 72).

e. Raising/Lowering Mechanism

The lowering of the transducers and sources may be accomplished through air cylinders 52 (FIG. 2). A cylinder-mounted spring counterbalances the transducer weight and part of the source weight so that active pressure is required only to lower the mechanisms. Transducer and source-lowering cylinders 52 and 54 are tied to electrically controlled solenoid valves 66 that are software controlled by computer 24 (FIG. 1). These valves connect cylinders 52 either to outside air or to pressurized air when not activated.

Pressure to the lowering mechanisms is preferably provided by mechanical regulators, thus requiring adjustment only after major modifications or repairs.

f. Sources

As shown in FIG. 3, each source 32 consists of accumulator chamber 67, computer-controlled firing solenoid 66, and spring-return air cylinder 69. Air from supply tank 22 fills the accumulators through common regulator 64. Upon receiving a signal from computer 24, solenoid 66a turns on briefly (several tenths of a millisecond) and allows the air from accumulator 67 into hammer cylinder 69. When solenoid 66a turns off, cylinder 69 is connected to outside air pressure, spring 71 retracts hammer 73, and accumulator 67 refills.

Solenoid valve 66a is preferably mounted directly on hammer cylinder 69. Accumulator 67 is preferably mounted as close to valve 66a as physically possible to minimize time delays and pressure losses associated with propagation of air-pressure transients.

Accumulator 67 preferably provides a high volume (several cylinder volumes) of pressurized air that may be moved quickly into cylinder 69 to provide rapid hammer acceleration. This action isolates the hammer movement from regulator flow restrictions caused by distance from air supply 22.

The cycle time for the hammer stroke and preparation for the next stroke may be controlled by pneumatic line size, accumulator volume, and regulator flow rate. Using conventional 6 mm connections and pneumatic lines, cycle times may be less than one second and are typically longer than the data acquisition/processing phase.

g. Source Feedback Control

Two factors are important in controlling the hammer hit: the force of the impact and the duration of the impact. The ideal situation is to have the shortest impact time at a controlled force level. Impact times and force levels are influenced by external conditions such as pavement or asphalt stiffness, surface condition, and temperature.

Three controls are available over the hammer behavior. The first is the duration of the solenoid opening that determines both applied force and pulse duration. The second is the initial height of the hammer above the pavement, which is manually adjusted. The third is the composition of the tonal head 103 on the hammer heads, which controls the frequency range input to the pavement through the source. Tonal head 103 is, for example, a removable rubber hammer head, which may be of a variety of hardnesses of rubber. A harder rubber gives a higher-frequency tone or tap, whereas a soft rubber head gives lower-frequency tones.

According to the present invention, a computer feedback loop shown in FIG. 4 is used to control the hammer hit characteristics. The digitized load-cell signals 102, 104 are compared with an expected load-cell signal 110 at conditioning block 86. When the digitized load-cell signal quality falls outside the desirable limits, computer 24 will adjust the solenoid opening duration and repeat the hit to either increase force, decrease force, or eliminate hammer bounce. If these adjustments are not adequate, then the operator is advised by computer 24 of the degraded signal quality and repairs are suggested.

2. Electronic Components

This section on the electronics of the Seismic Pavement Analyzer gives a general description of the circuits that are not purchased as systems from other vendors and must be custom built. The circuits may be built on printed circuit cards mounted inside the personal computer (PC) 24a of computer 24.

a. Schematic

A general schematic of the total electronic system, including interface with the computer, is shown in FIG. 4. Transducer signals collected on the trailer are indicated in the upper right of block 81. The trailer electronics include load-cell routing 110, temperature conditioning 112, source control buffer 116, control line buffering 114, and compressor switching 118. Analog signals are run through accelerometer and load cell conditioning stage 86 and geophone conditioning stage 90 located in tow-vehicle control electronics 80, and then go into analog multiplexer 88, which routes a computer-selected subset of 4 of the 12 signals through to programmable gain stage 84 and into analog-to-digital (A/D) board 24b. A distance measurement is also input through serial port 27 to computer 24 through serial port from a distance-measuring device 29, which may be a commercially available device such as an AMU™ 2000 meter. Hardware diagnostics circuit injects a known signal into signal-conditioning circuits 86, 90 so that overall circuit functions may be tested and compared with ideal responses. Also included in trailer electronics 81 are trailer lights 120.

The complete electronic package depicted in FIG. 4 may be run from a 110 V AC conditioned inverter 98 connected to the 12-volt system 100 of the tow vehicle.

b. Signal Conditioning

Figure 6:
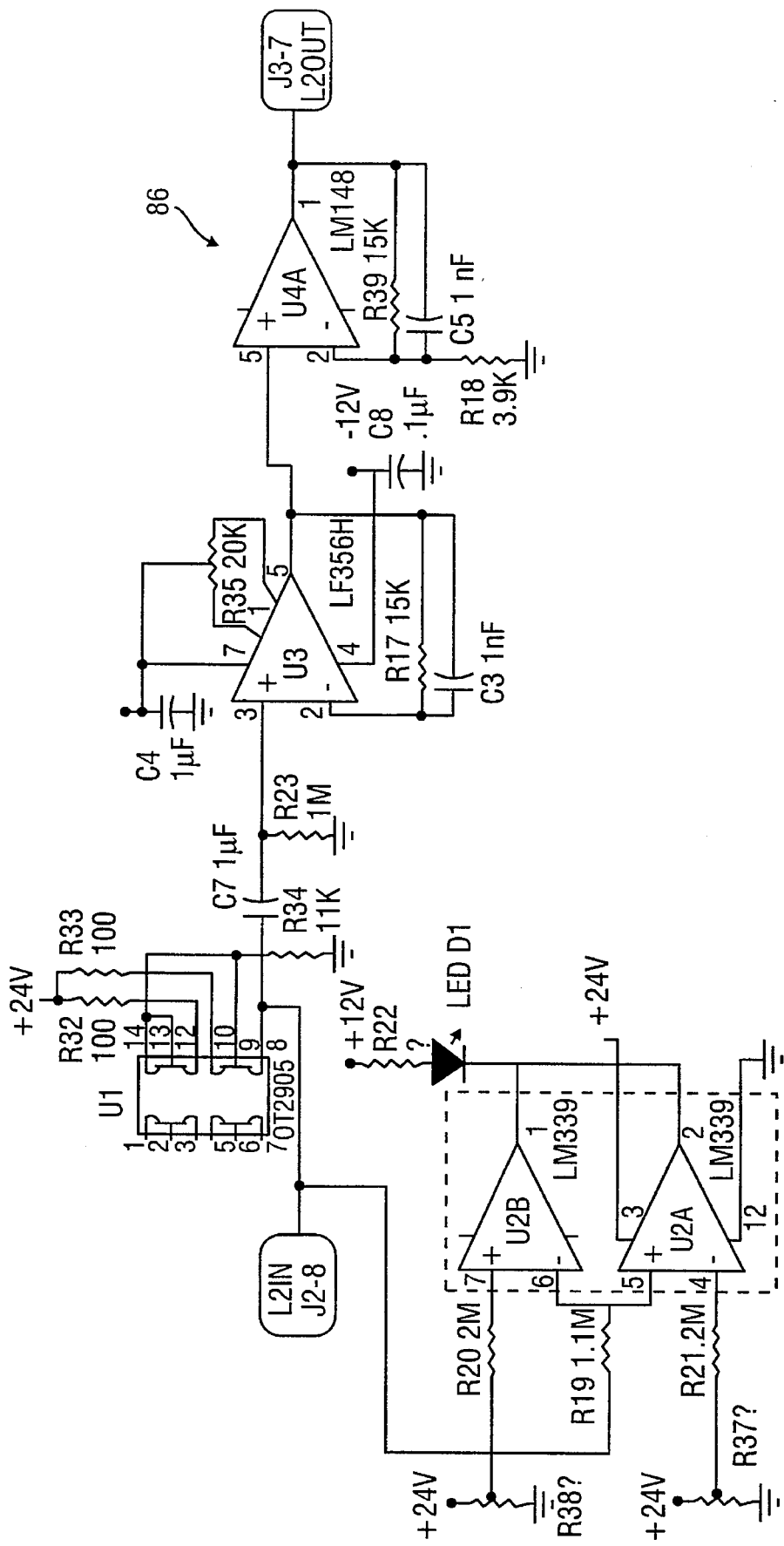
FIG. 6 is a schematic of sensor amplifiers for a seismic pavement analyzer according to the present invention.

The signal-conditioning circuits include thermocouple conditioning 112, accelerometer power supplies and amplifiers 86, geophone amplifiers 90, as well as regulator conditioner 96. Thermocouple conditioner 112 may comprise a single specialized integrated circuit with preferably better than one degree centigrade accuracy, such as an Analog Devices 596 device. The accelerometer and load cell signal conditioners 86 consist of line-condition warnings, two operational amplifiers with an input buffer, independent gain, zero offset, and 50 kHz anti-alias filters, as shown in FIG. 6. The geophone signal conditioning 90 consists of two operational amplifiers with independent gain, zero offset, and 5 kHz anti-alias filters, as shown in FIG. 6A.

Figure 6A:
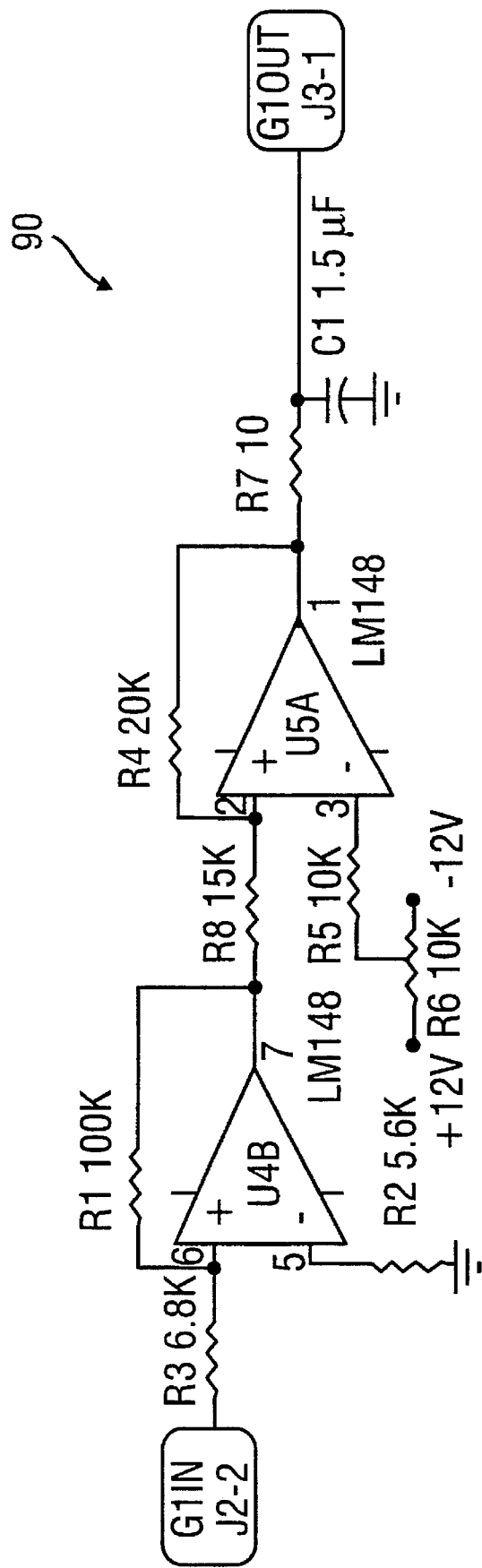
FIG. 6A is a schematic of a geophone signal conditioning circuit for a seismic pavement analyzer according to the present invention.

A channel of the geophone signal conditioning circuit 90 uses two operational amplifiers, U4B and U5A, shown in FIG. 6A. This amplifier gain may be adjusted by changing a resistor to account for different geophones that may be used in the system. The circuit converts the moderate geophone impedance to a low-impedance output signal that will not influence the analog multiplexer, includes output offset adjustment to maximize digitized dynamic range, and includes a low-pass filter to minimize high-frequency interference and aliasing.

A sample of the accelerometer and load-cell signal-conditioning circuits 86, shown in FIG. 6, uses two operational amplifiers (U3, U4A) for conditioning, a transistor array (U1) for a constant current source, and a comparator chip (U2) to monitor the accelerometer connections. The amplifier gain is also adjustable to account for different accelerometer sensitivities that might be used in the system. It also converts the high accelerometer and load-cell impedances to a low-impedance signal that will not influence the analog multiplexer. The circuit includes output offset adjustment similar to the geophone circuit and a low-pass filter to reduce high-frequency interference and aliasing in digitization. The accelerometer-monitoring circuit warns the operator when the accelerometer supply voltage falls above or below reasonable limits by turning on an LED (D1), corresponding to an open circuit or short circuit on the cable, respectively.

Exemplary component values for the circuit elements are given in FIGS. 6 and 6A. It is to be understood, however, that certain of these component values may be different for a given implementation of the present invention, and the values in FIGS. 6 and 6A are provided only for the purposes of describing a presently preferred implementation of the invention.

Temperature measurement circuit 112 consists of two thermocouples and cold-junction compensation. Temperature measurements are obtained from temperature sensor 33, which comprises ground temperature sensor 106 and air temperature sensor 108 (FIG. 1). This circuit serves as a reference potential and a very high-input impedance amplifier so that the analog multiplexer does not load the measurement. This signal conditioning may be performed by an Analog Devices AD564 chip, with no external components required.

The data acquisition hardware 24b may be, for example, a Metrabyte DAS-50 A/D board, which samples four channels at 250 kHz at 12-bit resolution. The Metrabyte PIO-12 has three parallel I/O channels that control and sense the electro-mechanical state of the Analyzer. These components are housed inside computer 24. Control line buffering circuits 94 and 114 provide buffering for data acquisition and for electronic commands from computer 24.

c. Multiplexer and Gain Control

For a four-channel A/D converter, as shown in FIG. 4, it is necessary to route subsets of the 12 input signals under computer control. The transducers may be divided into "banks" of 4 transducers per bank. For example, Bank 1 could be wired to read the high-frequency hammer load cell, and the near 3 accelerometers; Bank 2 could be the high-frequency load cell and the far 3 accelerometers; Bank 3 could be the low-frequency hammer load cell and 3 geophones; Bank 4 would then be the temperature transducers. Other configurations will be apparent to those of skill in the art based on the desired measurements to be made.

Analog multiplexer 88 takes a two-bit control signal (permitting selection of up to four banks) and routes one bank of 4 input signals to A/D board 24b. Multiplexer 88 is basically an electronically-controlled set of switches that are controlled by parallel input-output (I/O) board 24d in the computer 24.

Since the high-frequency load cell 102 and at least one accelerometer 42 are used in multiple measurements according to the present invention, these signals are preferably wired to be chosen in two banks. The temperature measurements occupy their own bank, and the low-frequency measurements occupy one bank. Signal strengths from the transducers may vary widely with pavement conditions so computer-controlled programmable gain 84 is included between multiplexer 88 and A/D board 24d. In order to take advantage of the full precision of A/D board 24d, the gain may be recursively adjusted using trial hammer hits and previous signal strengths to give an optimum signal-to-noise ratio.

d. Distance

Distance measurement is accomplished by counting revolutions of a transmission-mounted encoder wheel 28. Computer 24 queries the distance-measuring device 29 over an RS-232 serial port 27. Several vendors provide this type of equipment, and calibration of the distance should be performed to their specifications. An exemplary distance-measuring device is the AMU™ 2000 meter. This gives the operator of the SPA a single, calibrated, readable control for repositioning.

e. Internal Diagnostics

To assist in interchannel calibration and troubleshooting malfunctions, the capability to inject a known signal into the input of the signal-conditioning circuitry may be included. This function tests the signal conditioning circuits 86, 90, 96, 112, analog multiplexer 88, programmable gain 84, and A/D boards 24b for proper functioning. Implicitly, this also tests for failure of a transducer.

The data acquisition software has the option to switch signal-conditioning inputs to an optional computer-controlled pulse generator 92 if there is a need to test circuit operation. The resulting digitized waveform may be compared with ideal responses for each channel to help diagnose failures by eliminating all other possible sources of failure.

f. Computer Specifications

Exemplary computer equipment for data acquisition includes, for example, an i386 or i486 class of IBM-PC AT (or equivalent) computer with a floating-point processor and 4 megabytes of RAM, five expansion slots and two serial ports. If the data acquisition software is run on the same machine as data acquisition, a Hercules color graphics adaptor (CGA), enhanced graphics adaptor (EGA) or video graphics adaptor (VGA) graphics monitor and keyboard are preferred.

The user interface software of the Seismic Pavement Analyzer (SPA) may be run on an IBM-PC XT- or AT-equivalent computer (through port 82 shown in FIG. 4) with Hercules, CGA, or EGA/VGA graphics, 640 Kb ram, two 720 Kb floppy disk drives, with three serial ports. An AT with a hard disk and a floating-point chip would be highly desirable, but not necessary, to increase speed of operation in analysis-intensive operations. A 33 MHz, 80486 CPU may be used to speed up the Fast Fourier Transforms in data acquisition and to permit more extensive diagnostics to be made in real time.

The data acquisition and user interface computers may be separate, or may be combined into a single computer. B. Software Subsystems 1. Data-Acquisition Software Data acquisition according to the present invention is based on the concept of exchanging information through the user interface. The data acquisition software may be configured to look for Standard Input and Standard Output, which are flexibly reroutable ways to send data to the data-acquisition software or to an output device such as a screen or file. For example, reading Standard Input may entail receiving data from a keyboard, from a prewritten file, or from a distance over a modem (through port S2 in FIG. 4). Writing to Standard Output may entail writing to, for example, a file, modem, or to a screen.

A wide variety of software data acquisition options may be configured by data read in from a keyboard or external file. For example, the Standard Input file may be used to tell the acquisition software which measurements to collect (i.e., which of the available tests to perform). In addition, specific parameters may be input to the acquisition software every time data collection is initiated. Such parameters include the distances of each of the transducers 40 from their sources 32, the minimum number of hammer hits to use for each measurement, preliminary preamp 84 and A/D board 24b gains, preliminary hammer firing times, "baseline" digitization sample rate, and a definition of which transducer is connected to which bank and input channel.

Because many of the acquisition parameters have highly likely values, a set of defaults may be programmed into the acquisition software, with an ability for a input file to override those defaults if it is desired. However, for many of the acquisition option parameters, a wide range of unpredictable initial values is possible, and external definition is thus required.

Other types of optional configuring data that may be input to the software include minimum, maximum and expected values of thickness and stiffness of the pavement layers. In other words, design data for the subject pavement structure may be input to the software. These values may override the broad default values, which may cover all pavement types. The following expected measurements may then be calculated from the expected structure values: (a) expected paving layer shear modulus and density may be used to calculate the limits of the expected Ultrasonic-Surface-Wave velocity (Eq. (4)); (b) expected paving layer Young's modulus, shear modulus, and density may be used to calculate the limits of expected compression wave velocity (Eq. (3)); and finally, (c) expected densities, shear moduli and Young's moduli for the various sub-layers of the paving layer in turn may be used to calculate an expected dispersion curve for the Spectral-Analysis-of-Surface-Waves measurement method. These expected values may be used to provide quick checks on the accuracy of the measurement data retrieved.

2. Interpretation Software

The interpretation software according to the present invention is based on an inductive hypothesis-testing approach, using set theory. All distress-precursor hypotheses are tested by comparing moduli and thickness values with table-defined polygons. If a point falls within a polygon, the hypothesis is confirmed. If a point falls outside a polygon, the distance to the polygon is saved for comparison with distances for other hypotheses. If measurements are exterior to all polygons, relative distances are normalized to probabilities on each hypothesis.

3. Database-Management Software

Parameters collected by the data-acquisition hardware may be formatted for entry into a relational database manager (such as Borland's Paradox), under control of the user-interface software.

Five exemplary database tables that may be saved by the data-acquisition software are:

1. Moduli Values

Measurement ID

Young's Modulus, Shear Modulus, Thickness of Asphalt

Young's Modulus, Shear Modulus, Thickness of Concrete

Young's Modulus, Shear Modulus, Thickness of Base

Shear Modulus of Subgrade

Air Temperature, Ground Temperature

Densities

2. Time-Location

Measurement ID

Date

Time

Location

Equipment Serial Number

3. Error Messages

Measurement ID

Error

Error Source

4. Surface Wave Dispersion Data

Measurement ID

Curve fits and ranges on three segments

5. Compressional Velocities

Measurement ID

Four compressional velocity estimates between high-frequency load cell and four furthest accelerometers A measurement ID may be used to uniquely identify each set of data for each measurement location for later retrieval and analysis.

The database load and retrieve formats are preferably identical and are read by the interpretation software and quick-look graphical display.

With a relational database (such as that produced by Paradox), data may be retrieved into a spreadsheet (such as Borland's Quattro Pro). The spreadsheet may be used to perform summary computations and statistical calculations, and create graphs or reports. Data-retrieval-and-analysis scripts may be written in both the database and the spreadsheet to generate reports automatically that a particular highway department might desire. This eliminates the need for general purpose analysis, display, and reporting software.

C. Data Collection and Reduction

1. Data Collection

Figure 8:
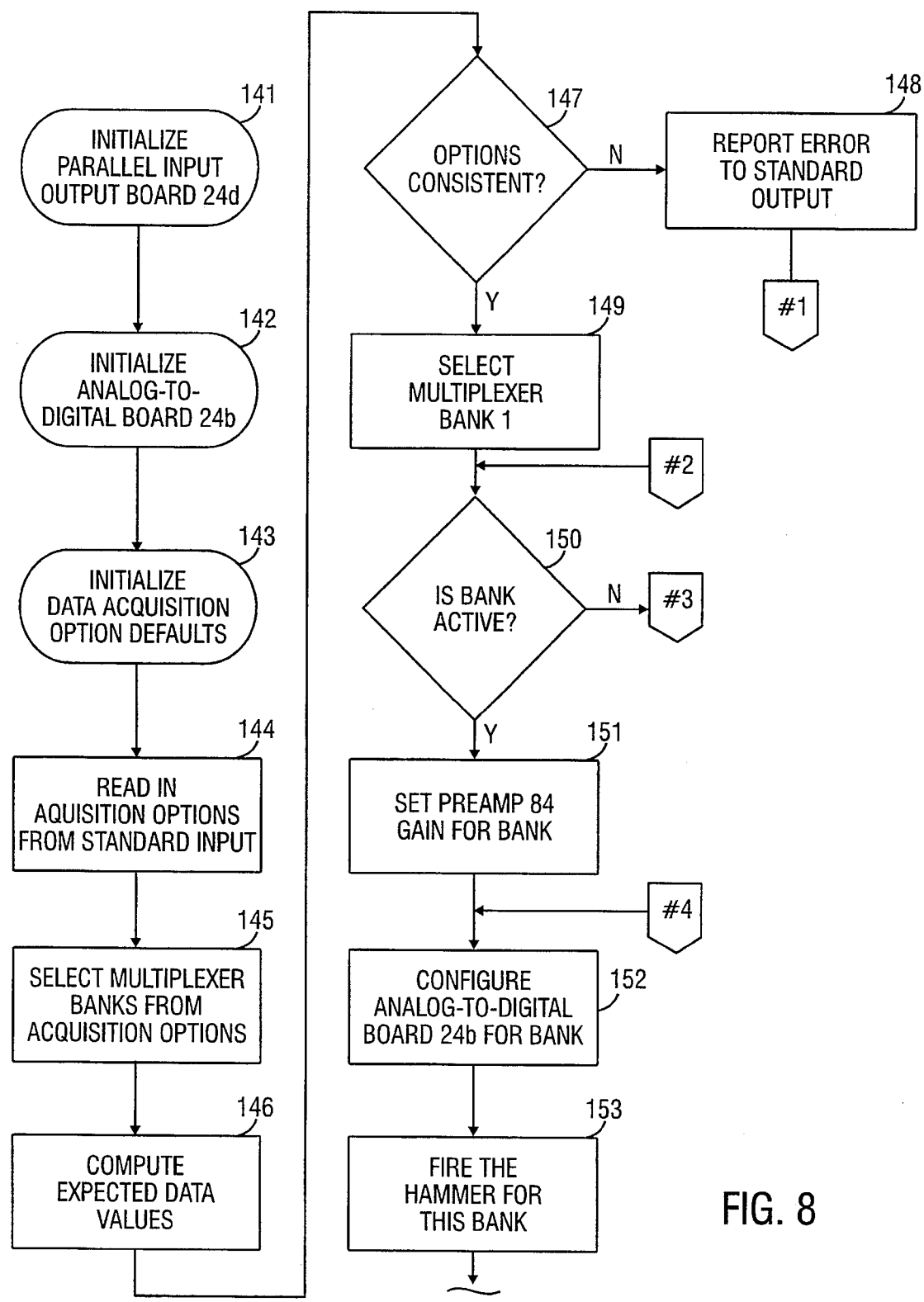
FIGS. 8–8C represent a flowchart illustrating a preferred method of seismic pavement analysis according to the present invention.
Figure 8A:
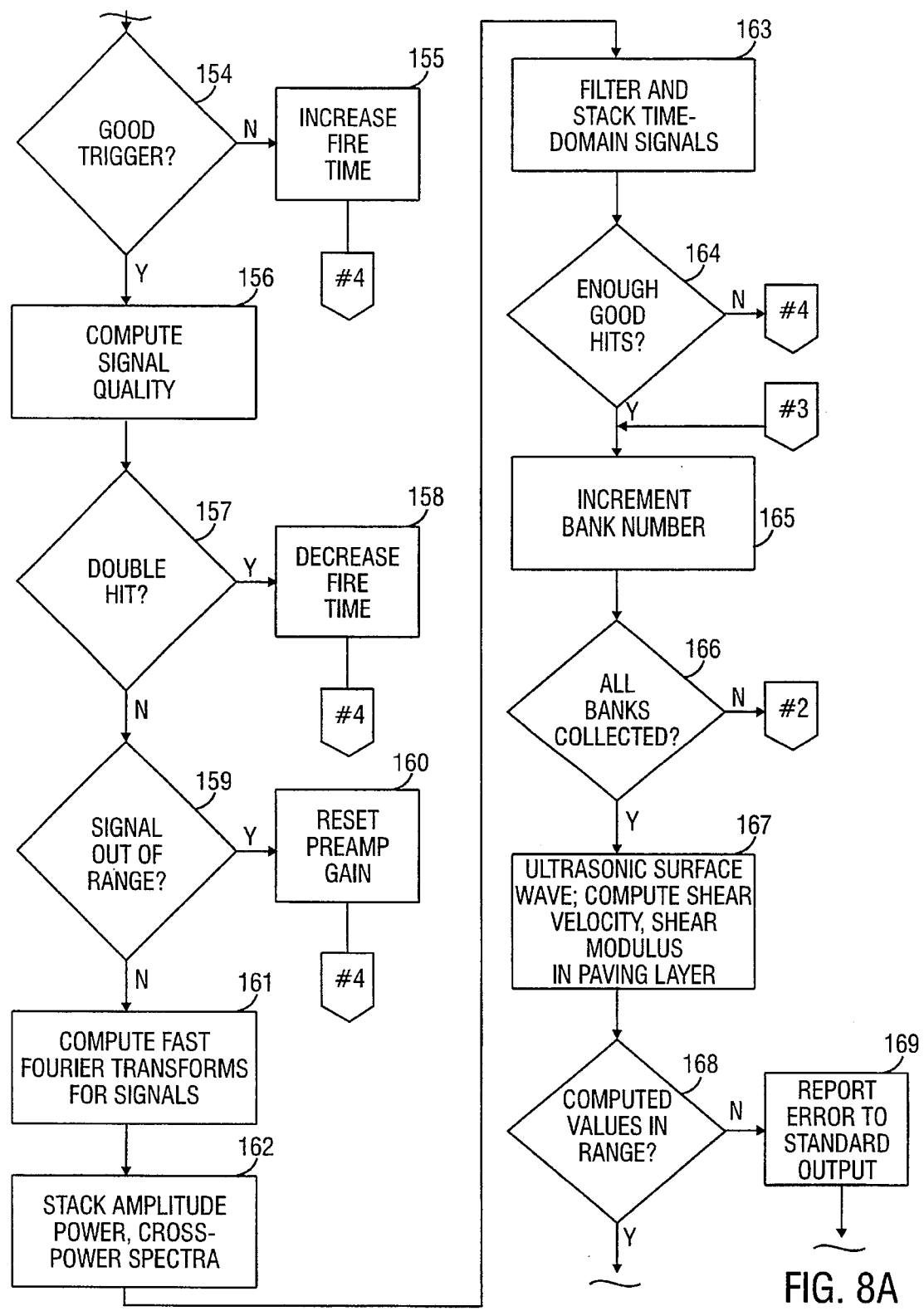
Figure 8B:
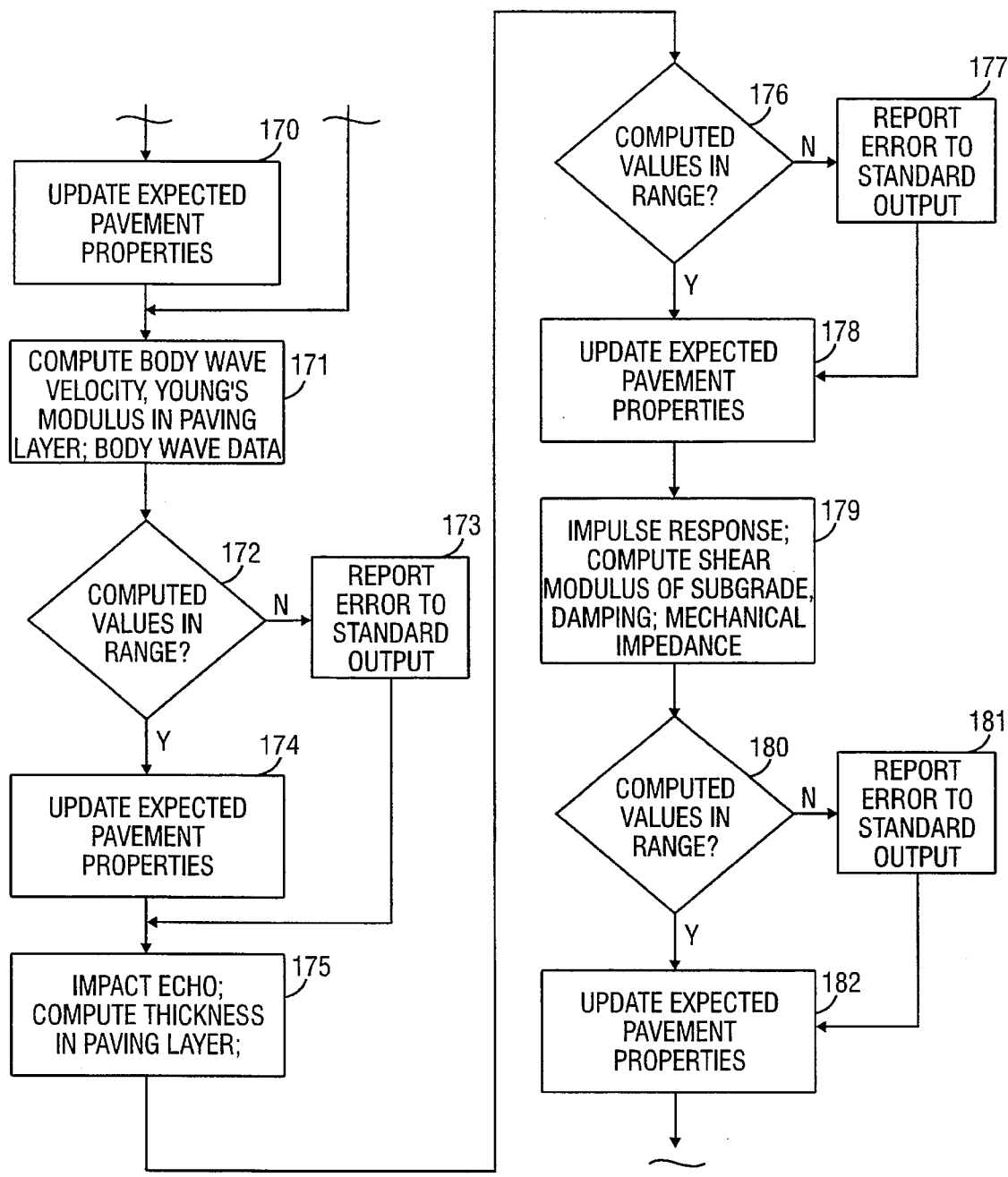
Figure 8C:
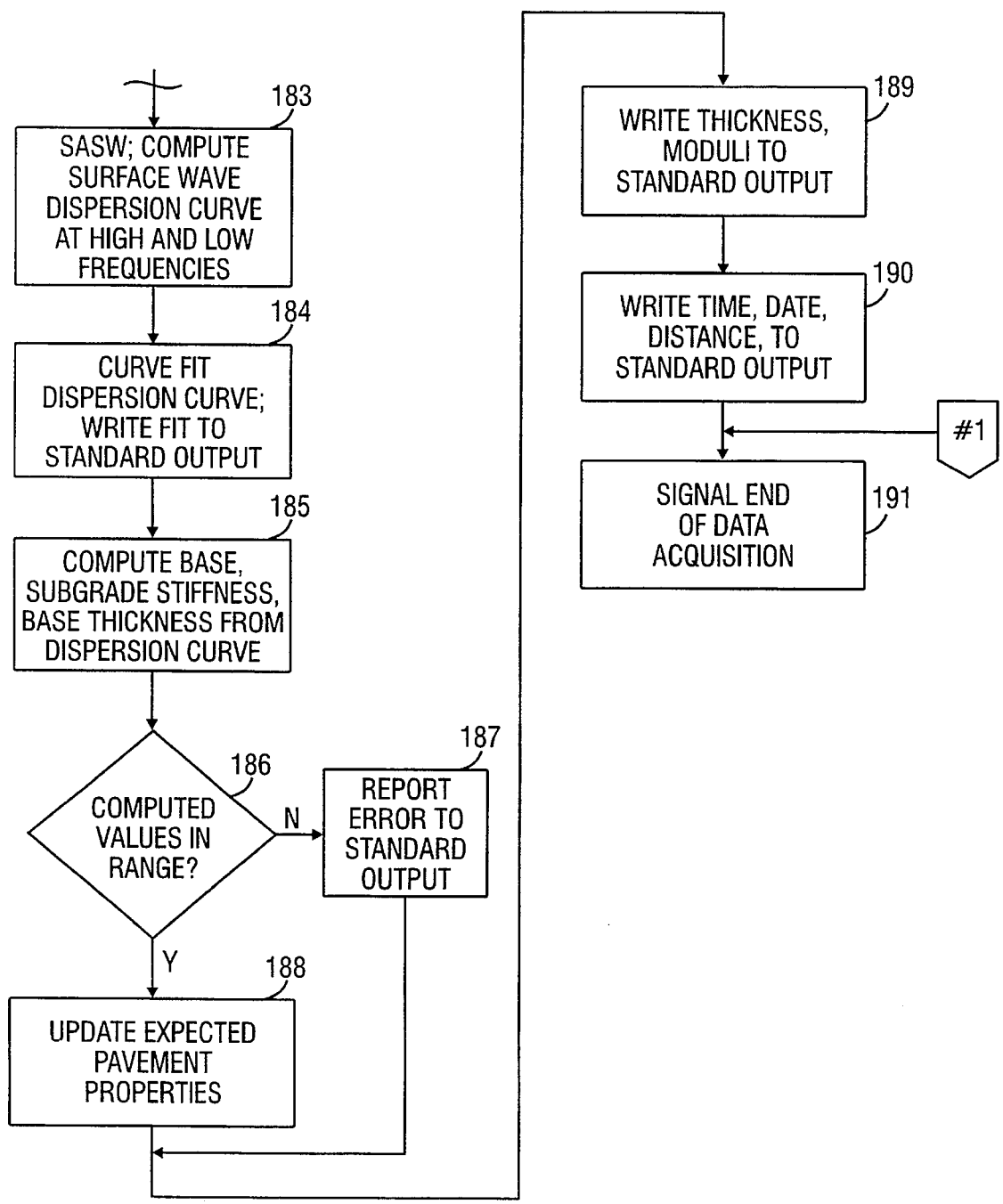

The activity sequence for a preferred method of operation of the SPA according to the present invention is presented in a flowchart in FIGS. 8–8C.

Prior to activation of the apparatus, computer 24 initializes the parallel input/output board 24d in computer 24 (block 141). The analog-to-digital board 24b in computer 24 is also initialized (block 142). Data acquisition default options, if applicable, are then read in from a default file or other suitable input device (block 143). The remaining software data acquisition options, such as which measurements to collect, etc. (discussed above) are then input to the system (block 144).

The technician initiates the testing sequence through the computer, which lowers the transducers 40 and impact sources 32 onto the pavement surface (FIG. 1). The appropriate bank of transducers is then selected for the first measurement to be made (block 145) based on the information derived from the data acquisition options (block 144). In the specific embodiment of the SPA disclosed in FIGS. 1–4, 12 sensors comprise transducers 40 (3 geophones 41 and 5 accelerometers 42), a high-frequency load cell 102, a low-frequency load cell 104, a ground temperature sensor 106, and an air temperature sensor 108.

Once the initialization data has been input to the computer 24, expected data values are computed (block 146). This process is discussed in more detail above. In a preferred method of operation according to the present invention, the acquisition options are then checked for consistency before the measurement process begins (block 147). For example, when the input data file requests measurement of the Impact Echo, the software accesses the bank and multiplexer channel number for the high-frequency load cell and the nearest accelerometer. If these values are not defined in the input file, or if they are defined in such a way that they cannot be measured simultaneously (e.g., if the transducer banks have not been properly defined to make this measurement), then the operation is terminated, and an error is reported to Standard Output (block 148). The end of data acquisition is then signalled (block 191), and the operator must correct the problem before that test may be completed. This checking feature avoids tying up the machine with needless operations for measurements that cannot be made.

If the acquisition options pass evaluation at block 147, the measurement cycles begin. The appropriate bank for the first measurement is selected (block 149). For example, if Impact Echo is to be measured, a bank consisting of the near accelerometers and the high-frequency load cell is activated. The gain for preamplifier 84 is set and the A/D board 24b is configured for that bank (blocks 151, 152). A source 32 is then typically fired four to seven times for best results. For the last three impacts of the source, the output voltages of the load cell and the receivers are saved and averaged (stacked) in the frequency domain (block The other (prerecording) impacts are used to adjust the gains of the pre-amplifiers (blocks 159, 160). The gains are set in a manner that optimizes the dynamic range.

After the bank has been fired, a series of quality checks may be made. For example, the trigger may be deemed acceptable (or "good") if the load cell used for the current bank rises above a set, adjustable level within set time limits after the hammer is fired (block 154). If the trigger is "good," signal quality for the signals received by the transducers is computed (block 156) by scanning the load cell signals for minimum and maximum values. However, if the trigger is not "good," then the fire time may be increased (block 155) and the bank may then be fired again.

Signal quality may be checked (block 156) by determining if more than one peak of the received transducer signal is 50% of the maximum signal. If so, then the signal quality is deemed acceptable. The signal may also be evaluated to determine whether the source made a double hit, which results from allowing too much air into the cylinder for the source. The extra hit degrades signal quality. If a double hit is detected, fire time is preferably decreased (block 158), and the bank is refired. The signal may also be evaluated to determine whether it is out of range (block 159). A signal may be deemed out of range if the transducer signals received were larger or smaller than expected. The preamplifier gain is preferably adjusted if necessary (block 160), and the bank is refired.

For the configuration illustrated in FIG. 4, fire time is the length of time parallel I/O board 24d electrically opens valve 66 to let high-pressure air flow into air cylinder 69 of either the high or low-frequency source 32a, 32b (see FIGS. 1, 3). The default initial fire time is set in the acquisition defaults (block 143) or the acquisition options (block 144). A typical fire time is between 35 and 45 milliseconds. An appropriate value by which to increase or decrease the fire time, if indicated (blocks 155, 158), is 5 milliseconds, but this value is arbitrary and any other suitable value may be chosen.

Once acceptable signals have been achieved for a given bank, the fast Fourier transforms are computed to transform the signals to the frequency domain (block 161). A fast Fourier transform takes a time or space bounded sampled signal and computes the amplitudes and phases of a discrete set of sinusoidal functions at a given set of frequencies. See Cooley, J. S. and Tukey, J. W., "An Algorithm for the Machine Calculation of Complex Fourier Series," *Math Computation*, vol. 19, pp. 297–301 (1965), the disclosure of which is herein incorporated by reference.

The amplitude, power, and cross-power spectra for the received signals are then summed mathematically by adding the sinusoidal amplitudes of each frequency (block 162). The cross-power spectra are obtained by multiplying two FFT transformed signals. Pairs are used for calculating the phase delay or dispersion between pairs of transducers.

For compression-wave analysis, the time-domain signals are then filtered to remove undesirable low-frequency elements, and the resulting signals are summed (block 163).

Figure 7:
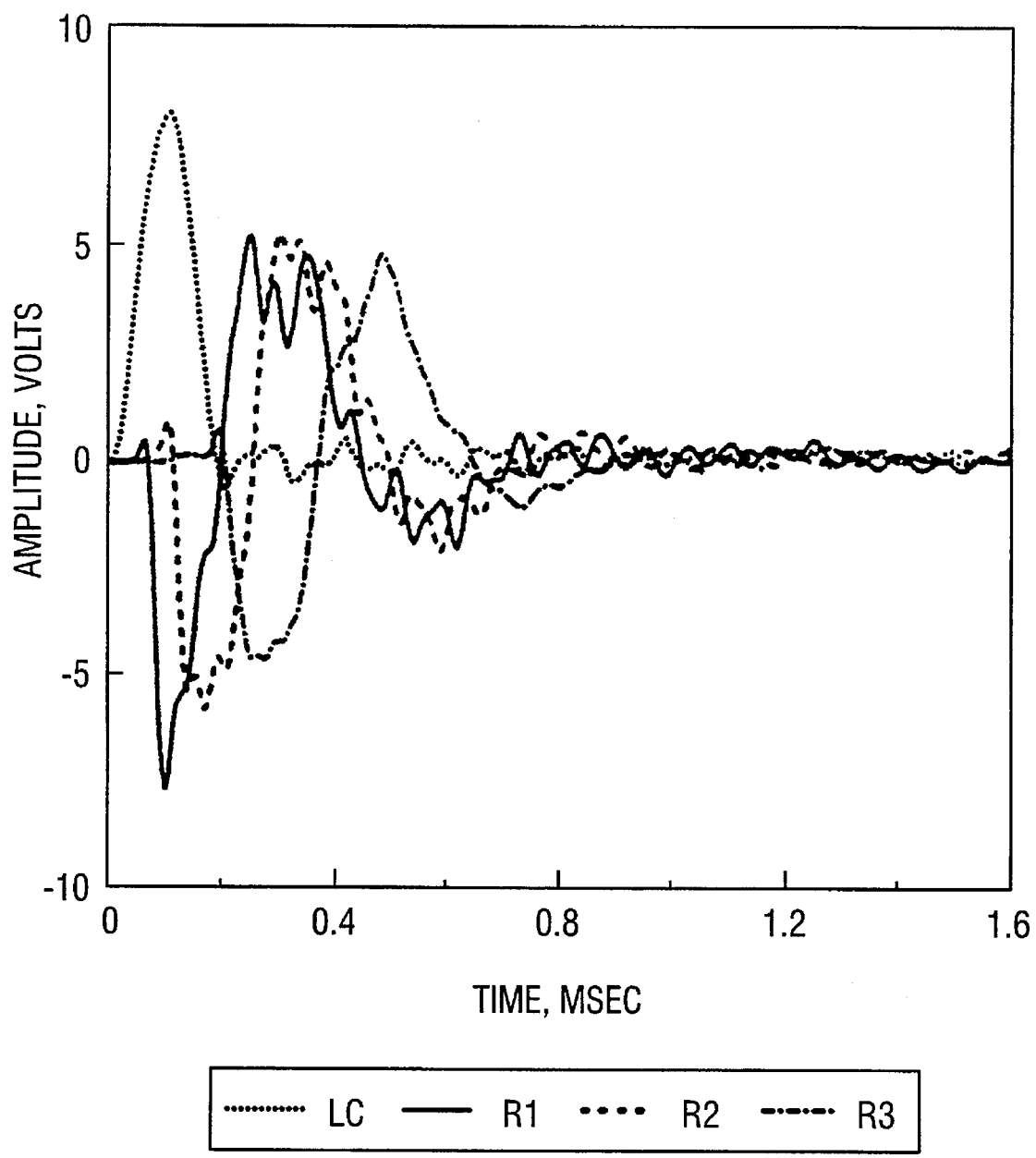
FIG. 7 is a graph showing typical time records from accelerometers and a high-frequency load cell according to the present invention.

Typical voltage outputs of transducers 40 are shown in FIG. 7 (illustrating the load cell and the three near accelerometers). Naturally, as the distance from the source increases, the amplitude of the signal decreases.

Figure 9:
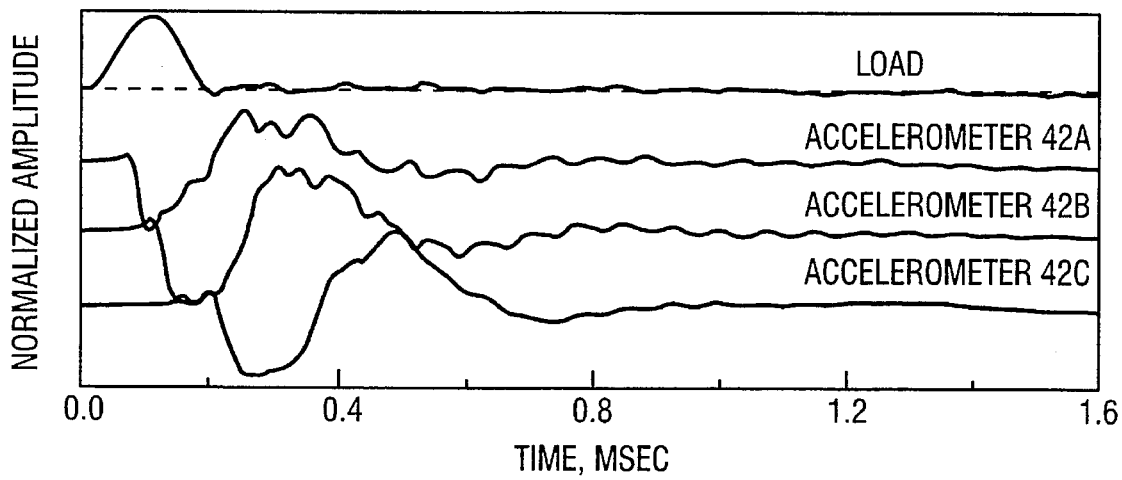
FIG. 9 is a graph showing normalized time records from near accelerometers and a high-frequency load cell according to the present invention.
Figure 9A:
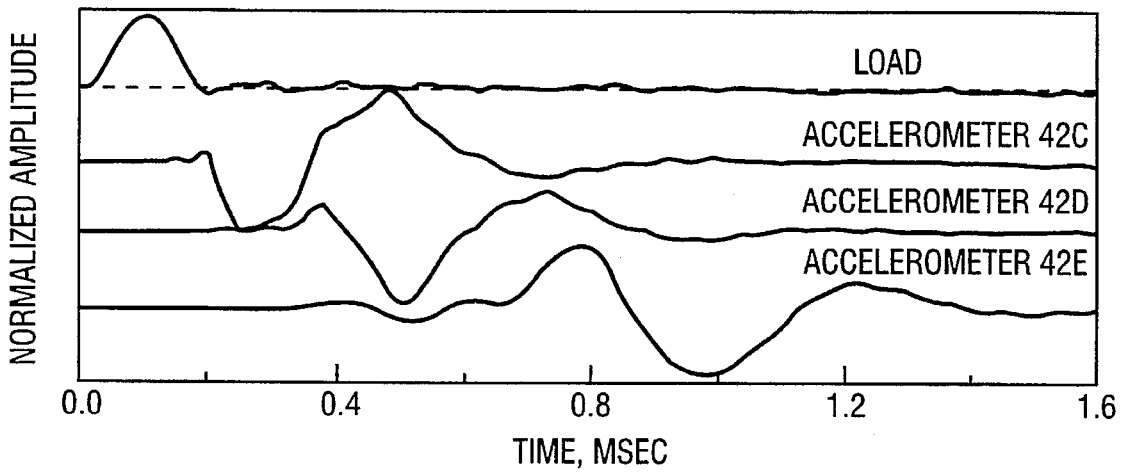
FIG. 9A is a graph showing normalized time records from far accelerometers and a high-frequency load cell according to the present invention.

To help ensure that an adequate signal-to-noise ratio is achieved in all channels, signals similar to those shown in FIG. 7 may be normalized to a maximum amplitude of one, as shown in FIG. 9. In this manner, the main features of the signals may be easily inspected. The signal-to-noise ratios shown in FIG. 7 follow the classic pattern of wave propagation in pavement layers.

Once the measurements for a particular test have been completed, the next bank indicated by the acquisition options is selected and initialized (block 165). The bank is then fired, and the resulting signals are then evaluated and transformed as described above. This process repeats (block 166) until all banks have been fired to gather all necessary data to analyze the subject pavement. Typically, each bank is fired enough times to collect 3 good hits (block 164). The data collected is then processed using signal processing and spectral analysis. These processes are described in the next section.

2. Data Reduction

The data collected in the manner described above are manipulated in several ways to determine the parameters enumerated in the Summary of the Invention. The rest of this section discusses the procedures for each testing technique.

a. Ultrasonic-Surface-Wave Method

This method determines the shear modulus of the top layer, using the time records of two accelerometers, such as accelerometer 42a (which may be, for example, 150 mm away from the source) and accelerometer 42b (which may be, for example, 300 mm away from the source) (see FIG. 9). These two signals are Fourier-transformed in a manner known in the art (block 161) and the ratio of the two signals is calculated in the form of the transfer function. (Box 167) However, this method uses only the phase of the transfer function.

Figure 12:
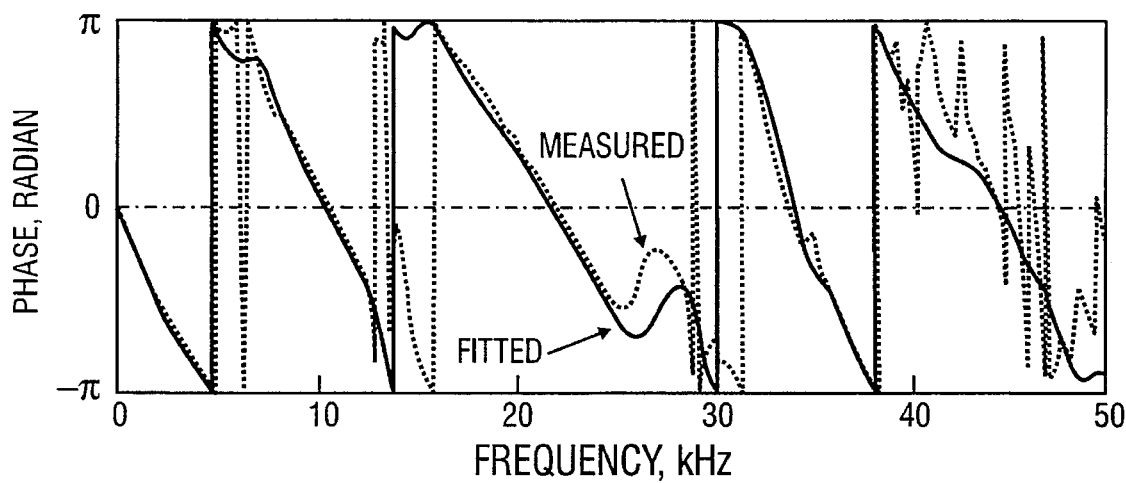
FIG. 12 shows a transfer function used in an Ultrasonic-Surface-Wave test (wrapped phase).
Figure 12A:
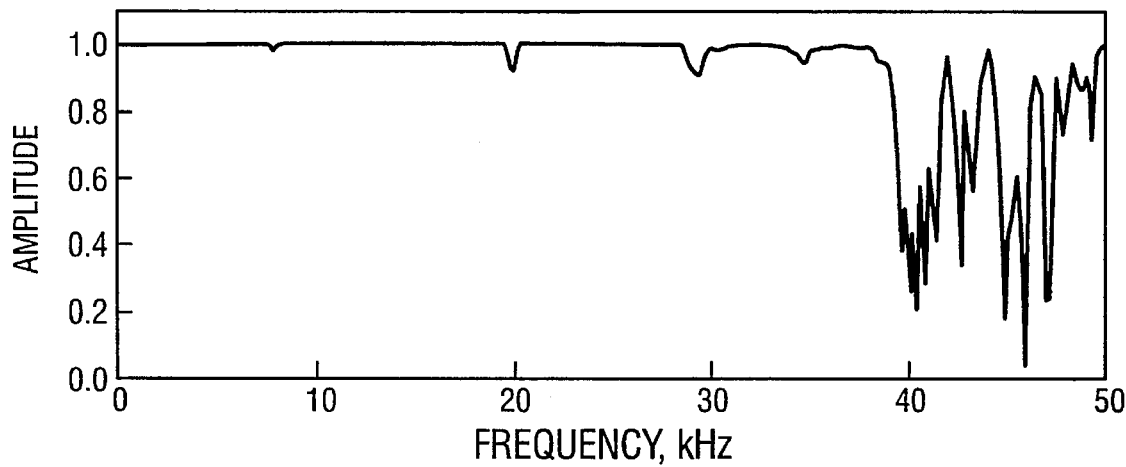
FIG. 12A shows a coherence function used in an Ultrasonic-Surface-Wave test.

A phase spectrum for time records similar to those shown in FIG. 9 is shown in FIG. 12. The phase oscillates on a radius between $\pi$ and $-\pi$ radians (180 and $-180$ degrees). This is the standard method of presenting phase data, because the detailed variation in the data may be observed in a small space. The coherence function associated with this record is shown in FIG. 12A.

The shear modulus of the top layer may be obtained using a complex-valued curve-fitting process with the coherence as the weighting function (block 167) (Eq. (13)). Representative results are shown in FIG. 12.

Figure 12B:
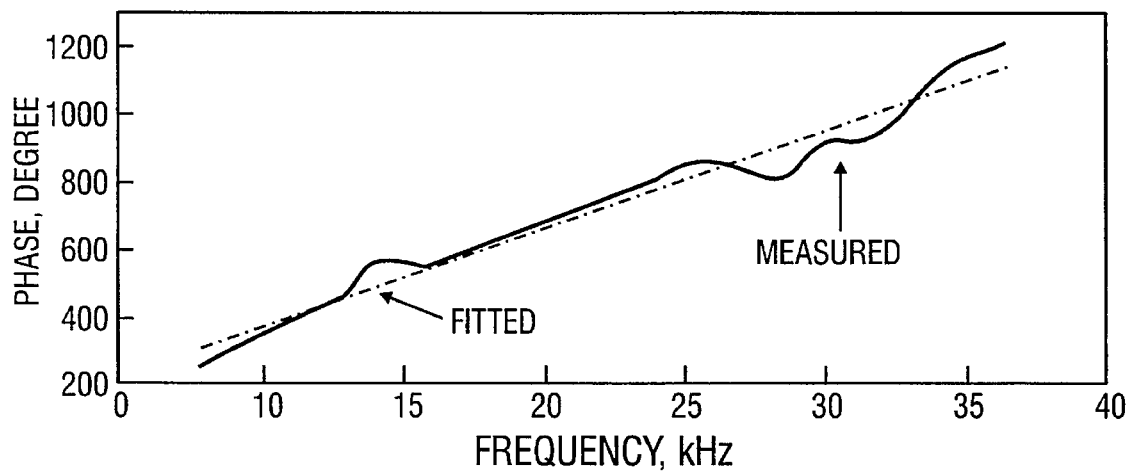
FIG. 12B shows a transfer function used in an Ultrasonic-Surface-Wave test (unwrapped phase).

In the next step, the phase is "unwrapped"; that is, the appropriate number of cycles is added to each phase. The transfer function for the "wrapped" phase shown in FIG. 12 is shown in FIG. 12B. The slope of the line is basically constant with frequency.

Finally, a line is fitted to the curve in the range of frequencies corresponding to wavelengths shorter than the thickness of the top layer. The slope of the line may be used to determine the shear modulus (see above) (Eq. (13)).

Once the shear modulus has been computed (block 167), the value obtained is checked to determine whether it is "in range." The range of values is predetermined by either acquisition defaults or the acquisition options input prior to initiating the measurements. If the computed values are not in range, an error message is reported to Standard Output (block 169).

If desired, expected pavement properties may be updated once the calculation is completed (block 170). As noted above, before the measurements begin, expected values may be entered. These may be derived loosely from a full range of possible pavements, or may be derived from the original design values for the particular subject pavement. These original expected values are updated as calculations are made, which involves replacement of the expected value with an average or a limit value, depending on the nature and quality of the measurement. For example, thickness is estimated in block 175 from the Impact Echo test (below), replacing a default or design value. A separate thickness is then computed in block 185. This thickness may be better or poorer quality than the estimate in block 175, as the two thicknesses are based on different measurements and properties and different qualities of data.

b. Ultrasonic-Body-Wave Method

Figure 13:
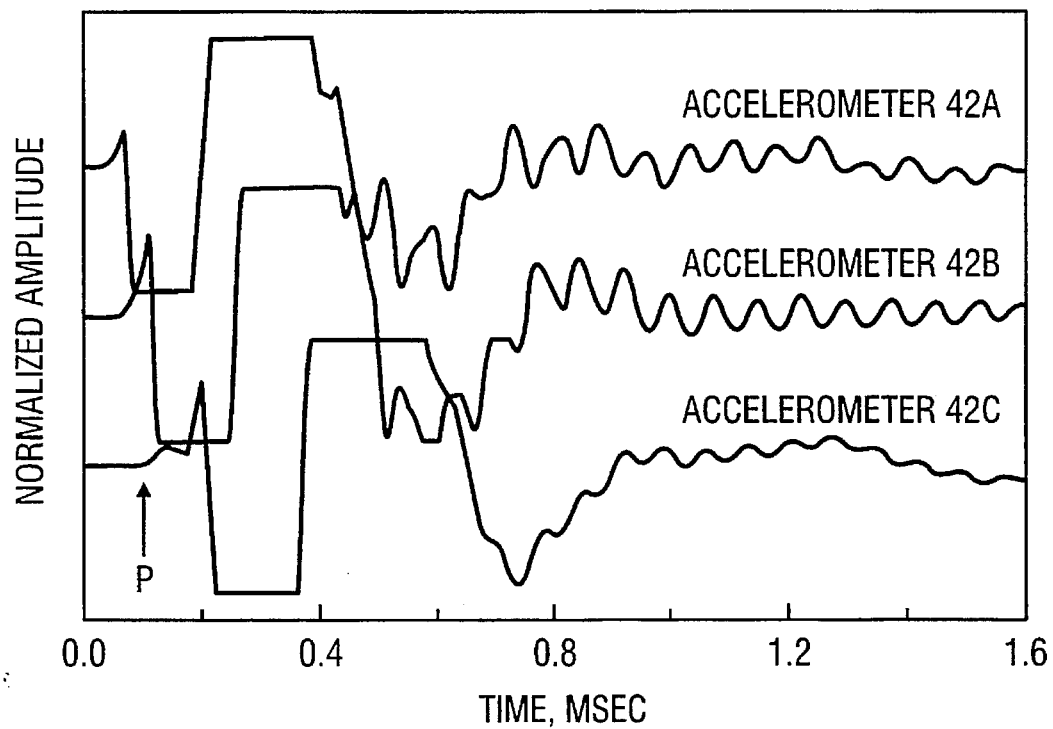
FIG. 13 shows typical amplified signals used in Ultrasonic-Body-Wave tests (near accelerometers).
Figure 13A:
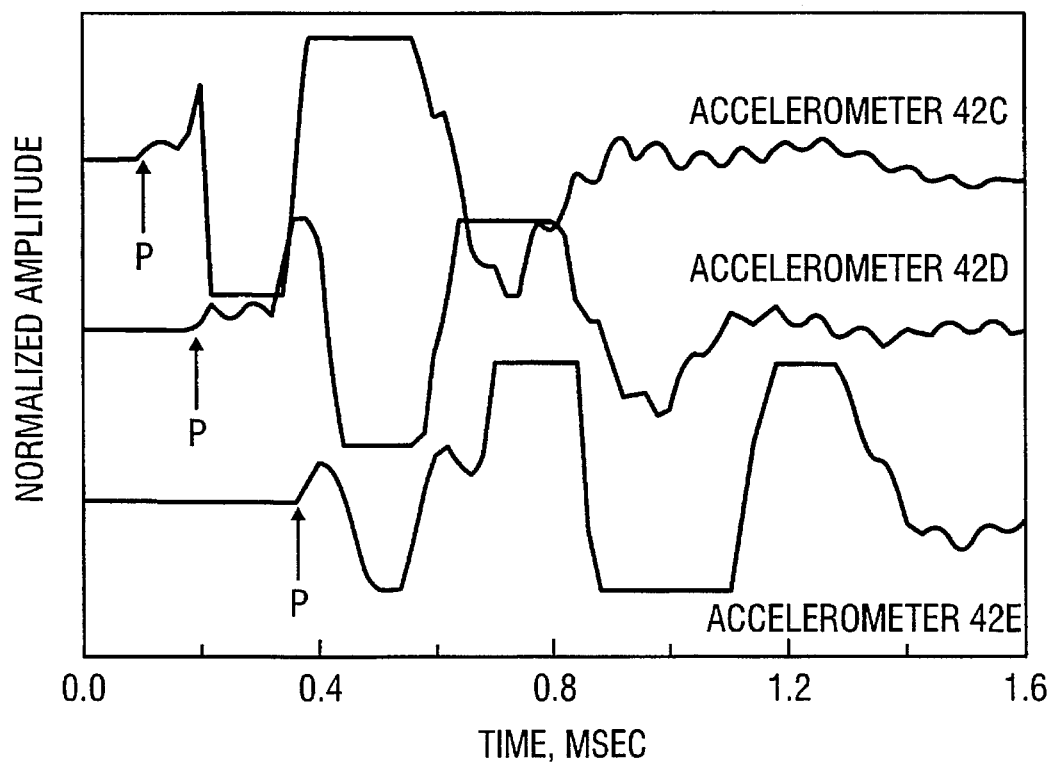
FIG. 13A shows typical amplified signals used in Ultrasonic-Body-Wave tests (far accelerometers).

The Ultrasonic-Body-Wave method uses the same data records summed time domain signals from block 163 as in the Ultrasonic-Surface-Wave method. In FIG. 9, the arrival of the body waves (compression waves or P-waves) cannot be identified in part because the surface wave energy dominates all signals. To determine the arrival of the P-waves, the gain of all amplifiers is set at the maximum possible range to collect data for determining compression wave velocities. (As discussed above, the necessary parameters are set in the acquisition options.) Such a record is shown in FIG. 13. Accelerometers 42a and 42b cannot identify the energy associated with the compression waves, because the seismic energy has not traveled over enough distance to separate into different types of waves (see above). However, the remaining accelerometers may identify the arrival of the P-waves. In FIG. 13, the arrows in each record correspond to the arrival of these waves; typically, accelerometers 42c and 42d record the arrival of energy most consistently (FIG. 13A).

To obtain the Young's modulus E (block 172), the difference in the arrival time between the two receivers is calculated. The primary wave velocity $V_p$ is calculated from the distance between the receivers and the difference in the travel time:

$$V_p = \frac{D}{\Delta t} \quad (16)$$

where

D=transducer spacing

Δt=time difference between transducers' receipt of signal. The compression wave (body wave) velocity may then be converted to Young's modulus E. See Eqs. (1), (6).

Once the calculations are completed, the values are checked against a predetermined range (block 172), and expected pavement properties are updated (block 174) unless the values are out of range, at which point an error message is written to Standard Output (block 273).

c. Impact-Echo Method

The Impact-Echo method (block 175) uses the records from the high-frequency load cell and the accelerometer closest to the high-frequency source. Typical outputs from the accelerometer and the load cell are shown in FIG. 9.

Figure 11:
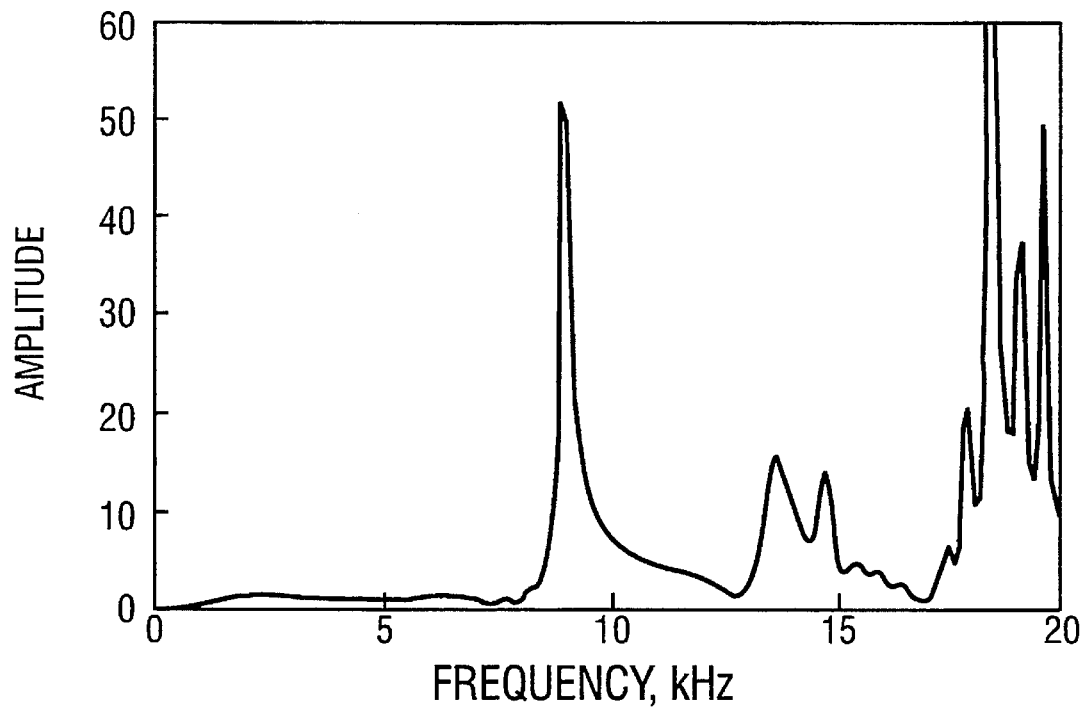
FIG. 11 is a graph of a typical flexibility spectrum used in an Impact-Echo test according to the present invention.

In the next step, the two signals are transformed into the frequency domain following the procedure outlined below for Impulse-Response testing (block 179). A typical frequency-response spectrum for a site is shown in FIG. 11. The major peak seen in FIG. 11 (at about 10 kHz) corresponds to the thickness of the layer and is called the return (resonant) frequency.

Figure 11A:
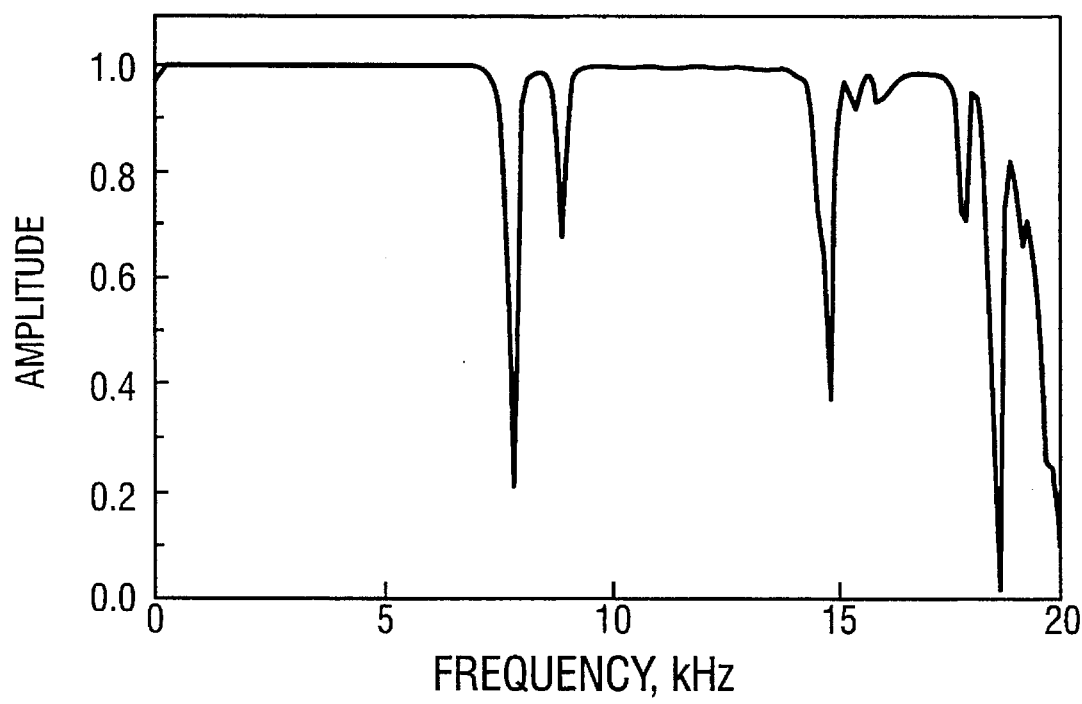
FIG. 11A is a graph of a coherence function used in an Impact-Echo test according to the present invention.

The coherence function is shown in FIG. 11A. In general, the data collected with the device have no incoherent noise, except at several isolated frequencies.

To calculate the thickness of the layer (block 175), the compression wave velocity of the material is determined using the Ultrasonic-Body-Wave method. See Eq. (3). The thickness T is equal to one-half of the ratio between the compression wave velocity and the return resonant frequency, as shown in Eq. (15).

Once the calculations are completed, the values are checked against a predetermined range (block 176), and expected pavement properties are updated (block 178) unless the values are out of range, at which point an error message is written to Standard Output (block 177).

d. Impulse-Response Method

Figure 9B:
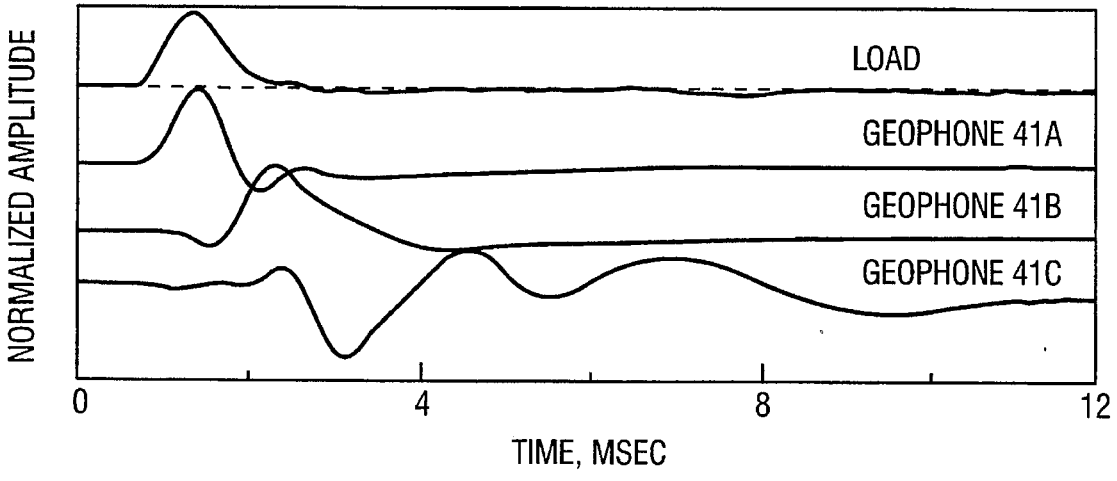
FIG. 9B is a graph showing normalized time records from geophones and a low-frequency load cell according to the present invention.

The Impulse-Response method (block 179) is similar to the Impact-Echo method. This method uses low-frequency source 32a to impact the pavement, and gathers the voltage output from a bank comprising first geophone 41a (FIG. 1) (the geophone closest to the source) and the low-frequency load cell 104. The results are shown in FIG. 9B. The shear modulus G of the subgrade is computed using Eq. (12).

A typical load cell record consists of a half-sine wave approximately 2 milliseconds long. The small reverberation past the actual impact corresponds to the reflection of the wave inside the source assembly. The amplitude of this reverberation is muted so it does not affect the results. The response of the geophone is a steady-state damped response. The slight time delay between the geophone and load cell records is the result of the separation between the source and the receiver.

The outputs of the low-frequency load cell and geophone are transformed into the frequency domain using a Fast-Fourier Transform (FFT) algorithm (block 161), obtaining the ratio of the velocity and the load at each frequency. This function, the mobility spectrum, is then integrated to obtain the flexibility spectrum. The flexibility spectrum is used to determine the parameters for detecting voids or loss of support. A typical flexibility spectrum is shown in FIG. 9.

Figure 10:
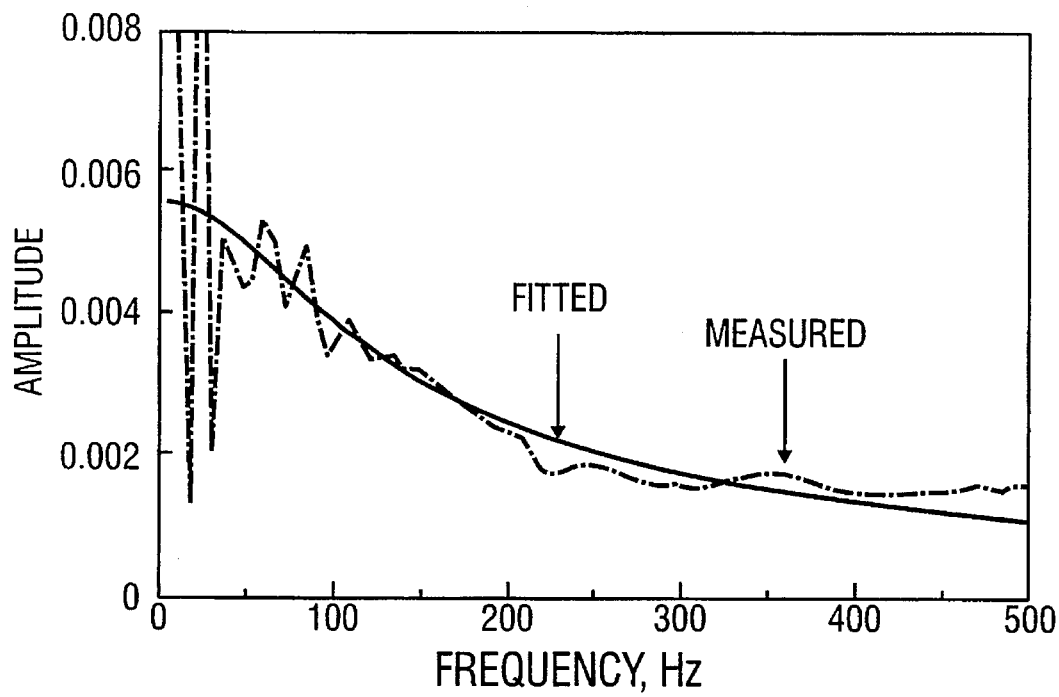
FIG. 10 is a graph of a typical flexibility spectrum used in an Impulse-Response test according to the present invention.
Figure 10A:
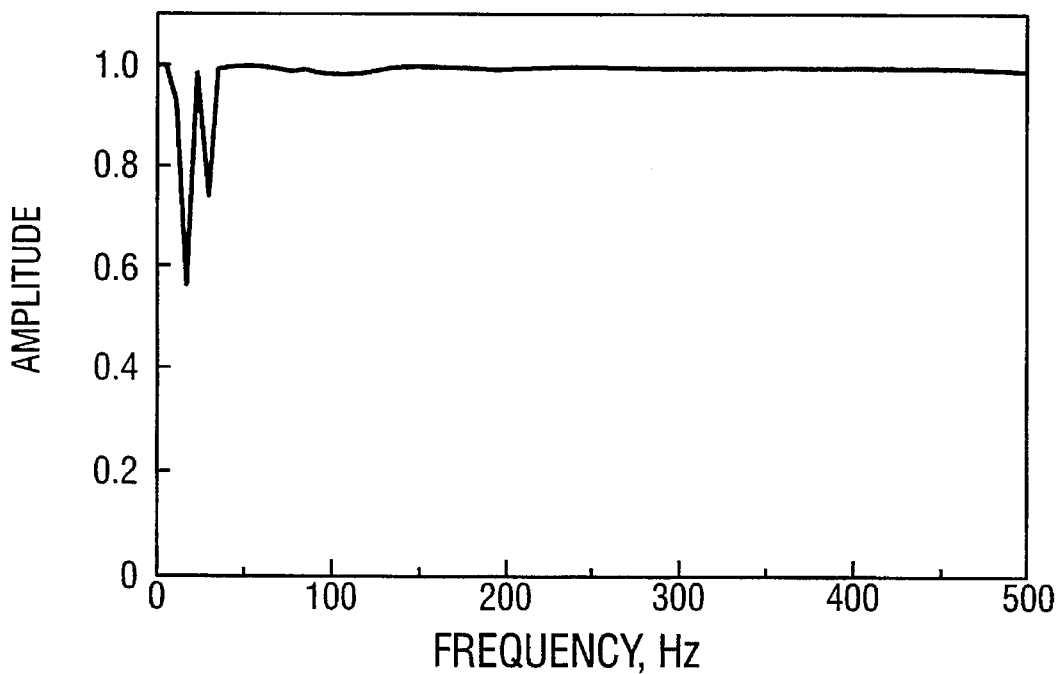
FIG. 10A is a graph of a coherence function used in an Impulse-Response test according to the present invention.

The coherence function associated with this record is shown in FIG. 10A. The coherence values are close to unity except at low frequencies. A coherence value of unity corresponds to a highly coherent signal between the load cell and receiver; i.e., no incoherent background noise in the signals.

In the next step, a complex-valued curve representing a single-degree-of-freedom (SDOF) dynamic system is fitted to the flexibility spectrum (block 179). A typical fitted curve is shown in FIG. 10.

Once the calculations are completed, the values are checked against a predetermined range (block 180), and expected pavement properties are updated (block 182) unless the values are out of range, at which point an error message is written to Standard Output (block 181).

e. Spectral-Analysis-of-Surface-Wave (SASW) Method

The two main goals of SASW testing are to obtain a dispersion curve and to invert the dispersion curve to obtain the shear modulus profile. Each step is briefly described below.

The initial steps involved in obtaining a dispersion curve are similar to those described for the Ultrasonic-Surface-Wave method (block 167). Time records from each two consecutive sensors are Fourier-transformed (block 161); spectral analysis is applied to obtain the phase information of the transfer function and the coherence function (block 162). The curve-fitting procedure described for the Ultrasonic Surface Waves is implemented; from the fitted phase spectrum, the dispersion curve (phase velocity versus wavelength) associated with that pair of records is determined (block 183). This process is repeated for all receiver spacings. Finally, the representative dispersion curve is obtained by combining the dispersion curves from different spacings using a known least-absolute-value best-fit (L1-norm) curve-fitting process. The details of this process may be found in, for example, Nazarian, S. and Desai, M., "Automated Surface Wave Testing: Field Testing," *Journal of Geotechnical Engineering*, vol. 119, pp. 1094–112 (1993), the disclosure of which is incorporated by reference. In the maximum likelihood estimate, the representative value would be the median of the data which is a robust representative of a group of data points. The outcome of this curve-fitting operation would be a polynomial curve. As soon as the polynomial coefficients are determined from the above curve-fitting process, the fitted dispersion data are obtained. A moving window averaging technique is then used to obtain between 20 to 50 representative dispersion data points which can be used in the inversion process.

Figure 14:
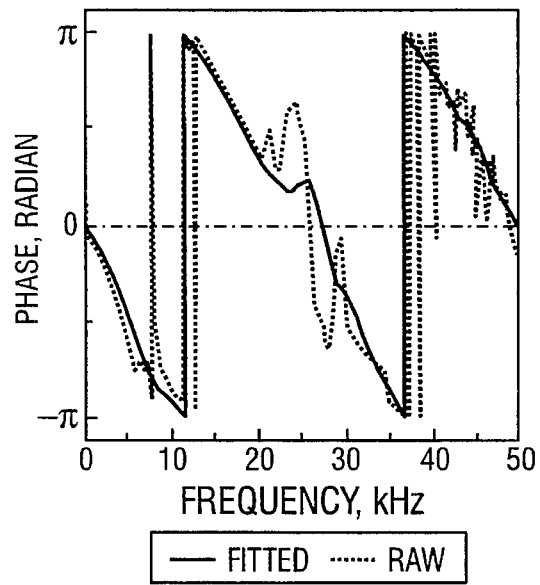
FIG. 14 is a graph showing typical phase spectral functions used in Spectral Analysis of Surface Waves tests (75 mm receiver spacing).
Figure 14A:
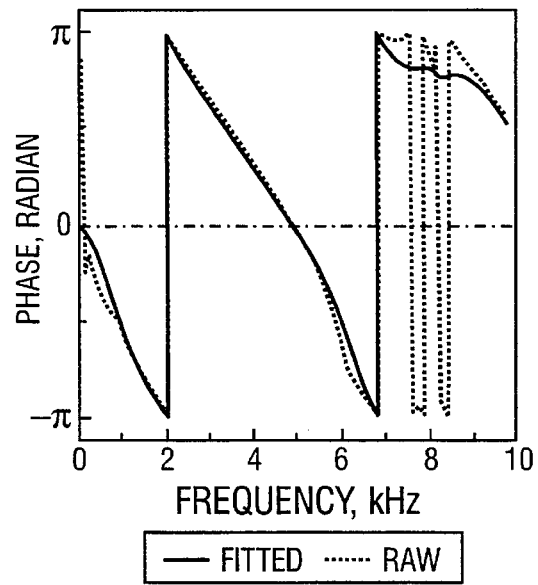
FIG. 14A is a graph showing typical phase spectral functions used in Spectral Analysis of Surface Waves tests (300 mm receiver spacing).
Figure 14B:
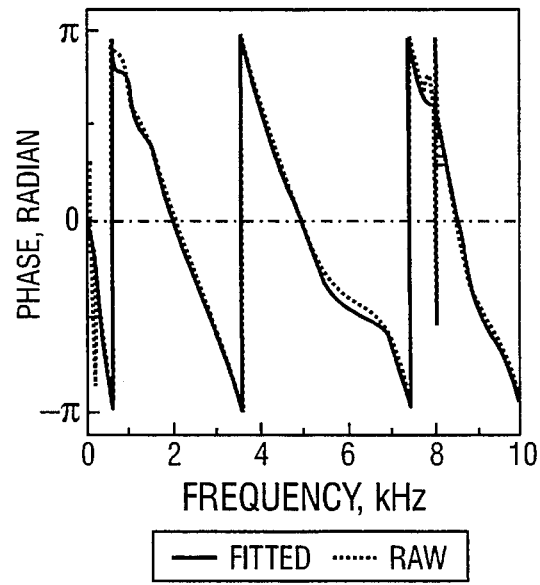
FIG. 14B is a graph showing typical phase spectral functions used in Spectral Analysis of Surface Waves tests (600 mm receiver spacing).
Figure 14C:
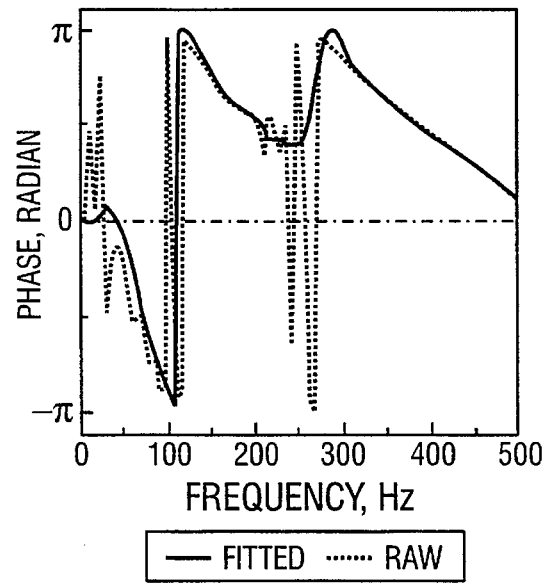
FIG. 14C is a graph showing typical phase spectral functions used in Spectral Analysis of Surface Waves tests (1200 mm receiver spacing).

The accelerometer records are used for near spacings. Four sets of phase spectra are utilized. These are phase spectra between accelerometers 42a and 42b (spacing of, for example 75 mm); accelerometers 42b and 42c (spacing of, for example, 150 mm); accelerometers 42c and 42d (spacing of, for example, 300 mm); and accelerometers 42d and 42e (spacing of, for example, 600 mm). An example of the phase spectra and the coherence functions for one test is shown in FIGS. 14–14C, where FIG. 14 represents 75 mm spacing, FIG. 14A represents 300 mm spacing, FIG. 14B represents 600 mm spacing, and FIG. 14C represents 1200 mm spacing.

In addition to the accelerometer records, two geophone records are used to obtain a dispersion curve associated with longer wavelengths. The example in FIG. 14 used geophone 41b (approximately 1200 mm away from the source) and geophone 41c (approximately 2400 mm away from the source). Also shown in FIG. 14 are curves fitted to the phase spectrum.

Figure 15:
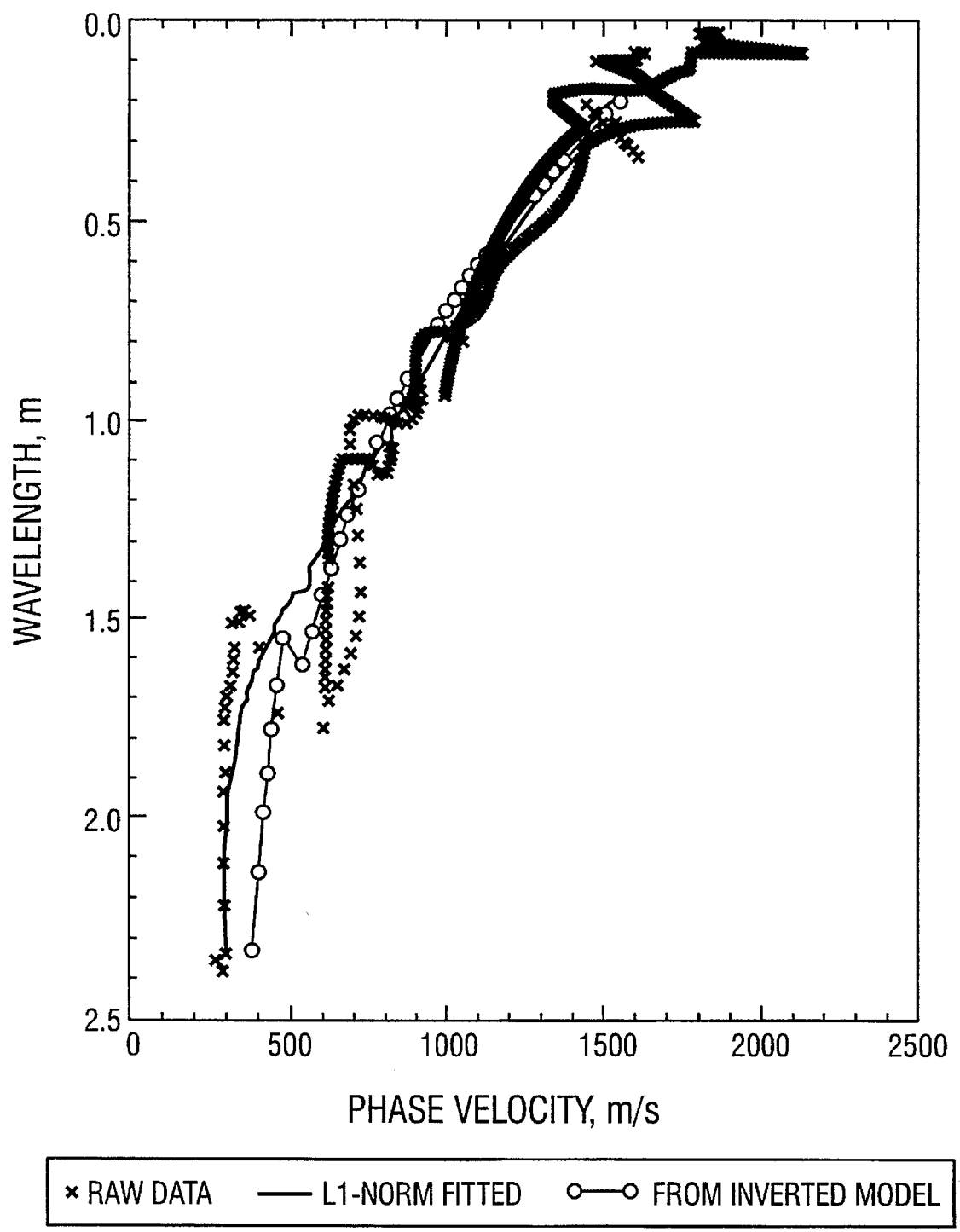
FIG. 15 shows a typical dispersion curve from a Spectral Analysis of Surface Waves test.

The next step is to determine the final dispersion curve (block 184). The dispersion curves obtained from all receiver spacings are combined as shown in FIG. 15. A curve is fitted to this data to obtain the "fitted-measured dispersion curve." This fitted curve is used in the inversion process. Shown in FIG. 15 is the fitted-measured dispersion curve obtained by the inversion process (termed "fitted" in the figure). The idealized curve is representative of the raw data.

Figure 16:
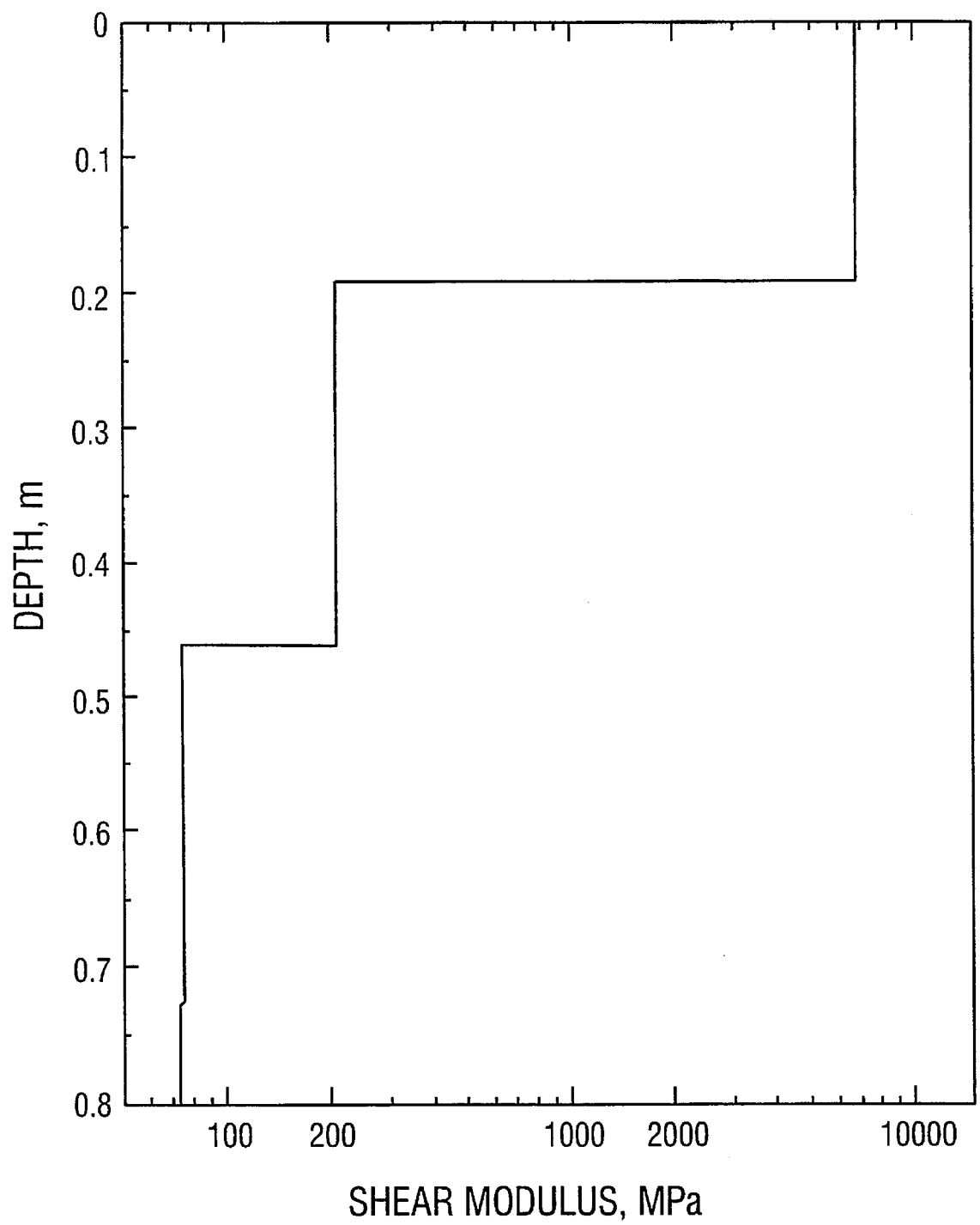
FIG. 16 shows a typical shear modulus profile from a Spectral Analysis of Surface Waves test.
Figure 17:
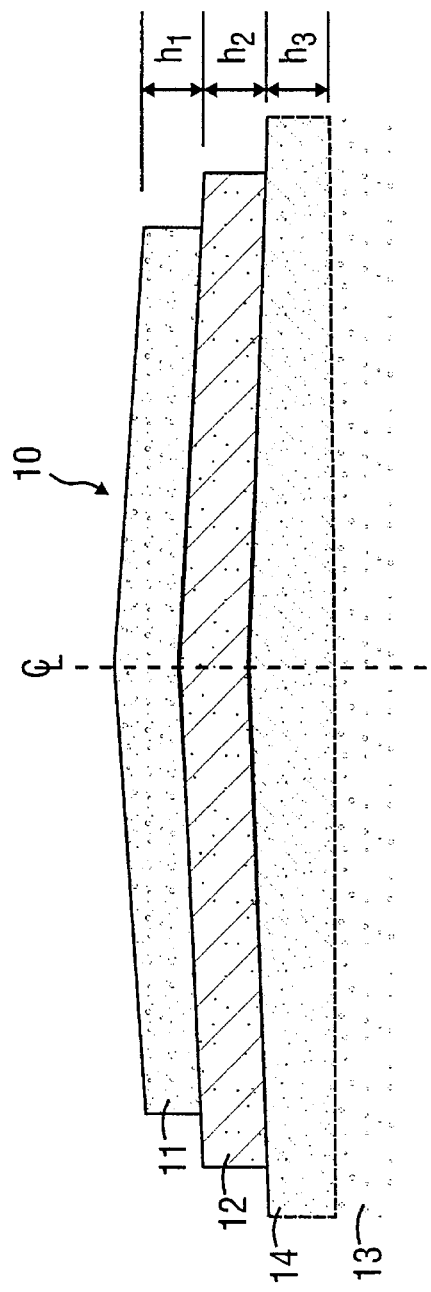
FIG. 17 shows a cross-section of layers of a typical flexible pavement.
Figure 17A:
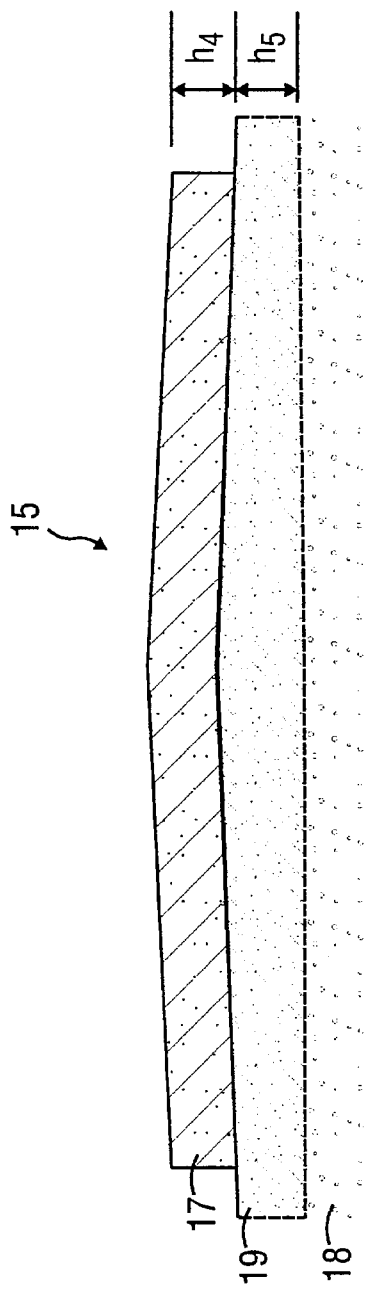
FIG. 17A shows a cross-section of layers of a typical rigid pavement.

Finally, an automated inversion process developed by Yuan, D. and Nazarian, S., "Automated Surface Wave Testing: Inversion Technique," *Journal of Geotechnical Engineering*, vol. 119, pp. 1112–26 (1993), the disclosure of which is herein incorporated by reference, determines the final Young's modulus profile for a site. The goal of the inversion process is to minimize the differences between the dispersion curve obtained in the field and a theoretical dispersion curve obtained from an assumed stiffness profile. To minimize the differences, the singular-value decomposition technique may be utilized. To overcome the nonuniqueness and/or instability in the solution, constraints may be applied based upon the conditioning of the problem and the error level of data. This effectively reduces some of the shortcomings of the standard (off-the-shelf) optimization technique. A sample Young's modulus profile is shown in FIG. 16.

To help ensure that the inversion process is successful, the fitted-measured dispersion curve is compared with the theoretical dispersion curve (obtained from the Young's modulus profile shown in FIG. 16) (block 186). This comparison is depicted in FIG. 15.

Once the calculations are completed, the values are checked against a predetermined range (block 186), and expected pavement properties are updated (block 188) unless the values are out of range, at which point an error message is written to Standard Output (block 187).

3. Results

Once the calculations for each of the foregoing methods are completed, the computed paving thickness as well as the shear modulus of the paving layer, the shear modulus of the subgrade, and Young's modulus are written to Standard Output (block 189). The time and date may also be written to Standard Output, as well as the distance from a reference point (block 190). The end of data acquisition is then signaled (block 191).

4. Interpretation and Diagnosis

Figure 18:
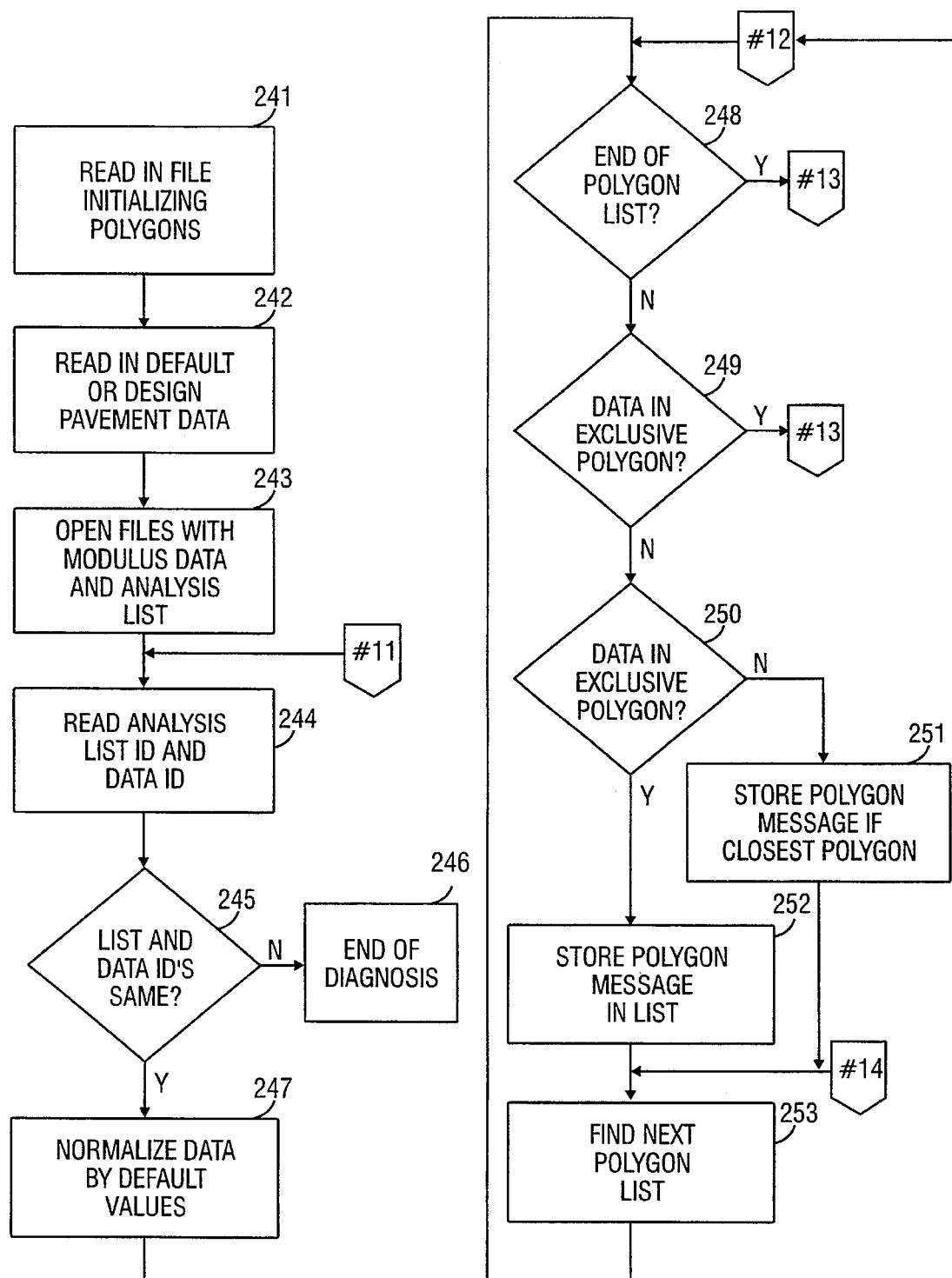
FIGS. 18 and 18A illustrate a flow chart of a preferred method of seismic pavement diagnosis according to the present invention.
Figure 18A:
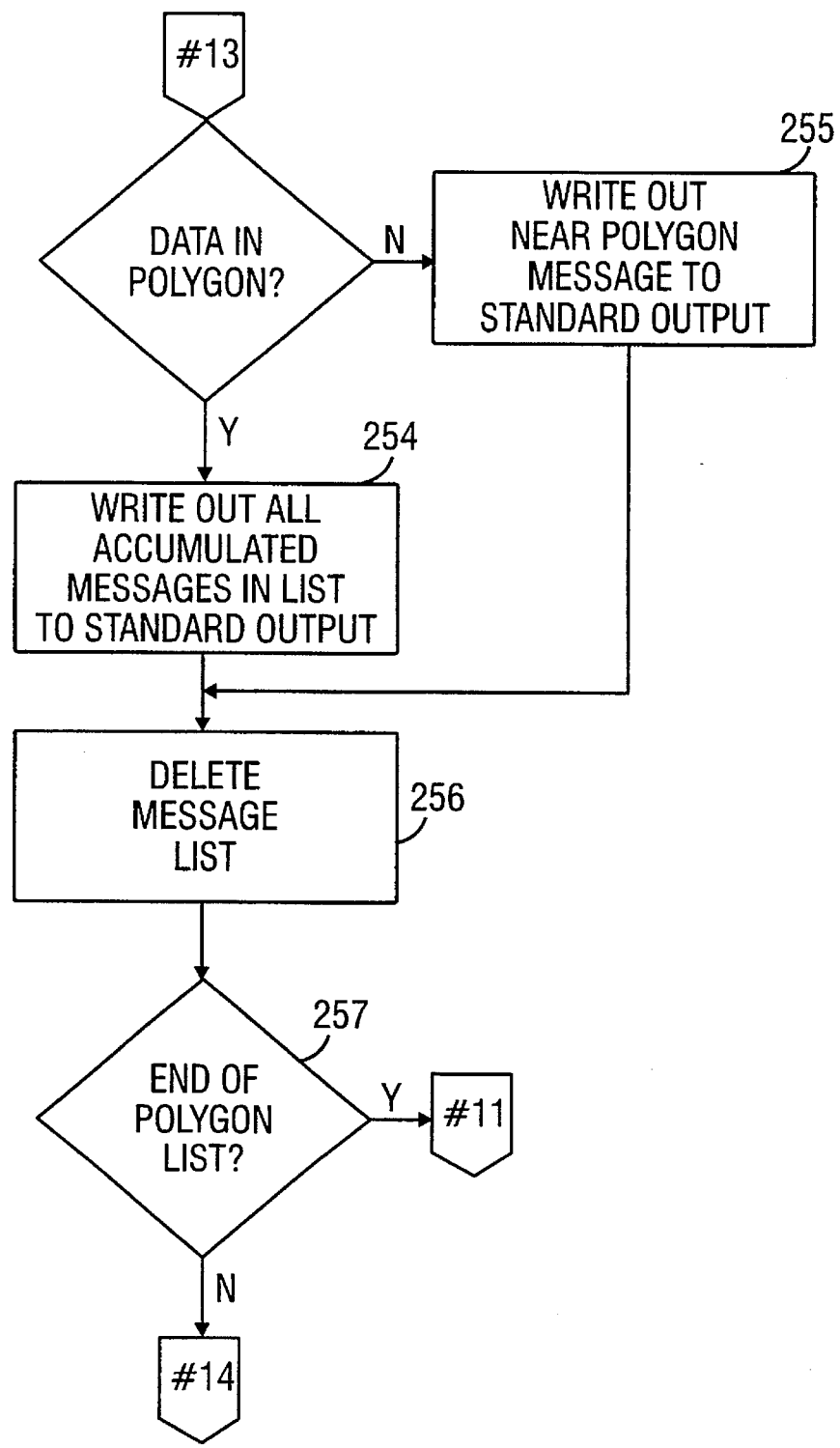
Figure 19:
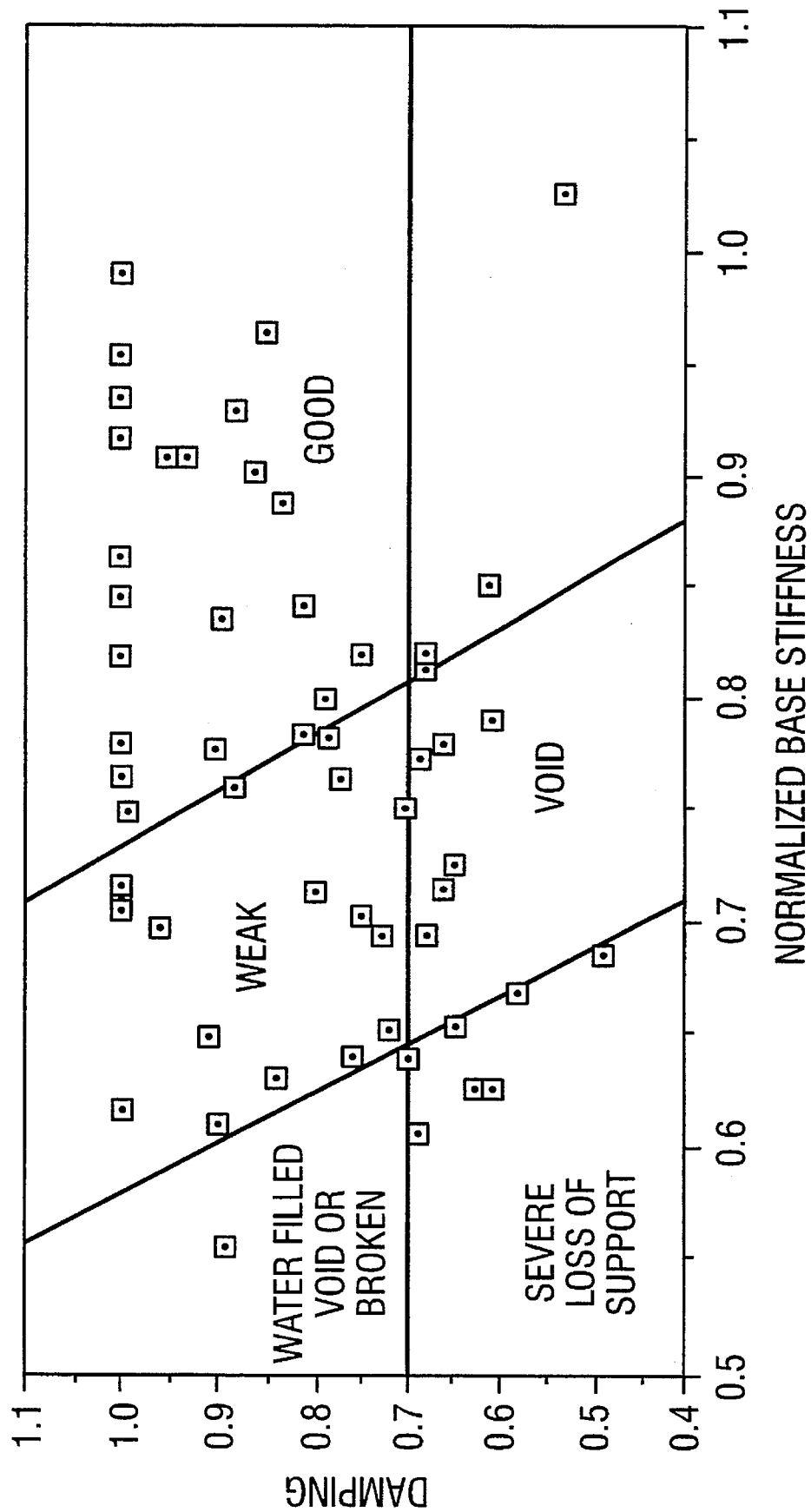
FIG. 19 shows an exemplary diagnosis polygon for determining base distress precursors according to the present invention.

According to the present invention, distress precursors are interpreted with a hypothesis-testing approach, relative to the design parameters for the pavement system. A flow chart setting forth exemplary steps in such a process is shown in FIGS. 18–18A. Each major distress type that may be detected by the device of the present invention has an associated relative-value polygon. Each polygon is derived from extreme values of parameters associated with the particular distress type. Each polygon list contains the names of the pair of data pints to be used in the analysis with a linked list of polygon vertices. Each polygon is classified by a level of importance (class), and by whether it is an inclusive or exclusive set. An example is shown in FIG. 19.

To begin the diagnosis of a tested portion of pavement, the initializing polygons and default or design pavement data are read in (blocks 241–42). The measured data and analysis (or index) list are then accessed (block 243). Each data file and analysis list is preferably coded with a unique ID (block 244), which are compared to each other (block 245) to verify that the proper data set is being analyzed. If the analysis list ID does not match the data file ID, the diagnosis is ended (block 246).

Next, the diagnosis involves normalizing measured data by default values based on design parameters of the pavement (block 247). The normalizing procedure continues until the full polygon list has been searched in an iterative loop (decision block 248). The first polygon on the list is then checked to determine whether it is inclusive or exclusive (blocks 249, 250). An exclusive set in a class means that only the one message will be returned from any polygon of that same class (blocks 254–56). Messages from inclusive sets of a higher rank will be returned, but all lower class polygons for that distress type are ignored. (This is determined in block 254 prior to writing accumulated messages to standard output.) If only inclusive sets are encountered, all messages corresponding to the selected polygons are returned to the user (blocks 250–54).

The measured values associated with the particular distress type are compared against the polygon to determine a relative value within the polygon, or within the extreme ranges. (See decision blocks 249, 250). For instance, if fine cracking exists, then Young's and shear moduli in the pavement will fall within a specified range of values that are a fraction of the ideal stiffness for the concrete type used. These ranges are predetermined based on knowledge in the field. For example, a high damping and high stiffness measurement for a base will indicate that the measured is "good," as it is known in the field that a base with a high damping factor and a high stiffness is deemed to be "good." See FIG. 19. If measurement points fall outside these ranges for known distress types, distances from the measurement points to the region will be used to weight the probability that the hypothesis is true (blocks 251, 255).

The diagnosis procedure may be a routine run optionally at the end of each data collection set-up, or on large sets of data from several measurement cycles, as defined in a list of data points for which diagnosis is desired.

The device of the present invention will preferably inform the user verbally or graphically of the evaluation of the paving layer with respect to the distress precursors under examination. Thus, in the preceding example, the device would return a suitable message to the user (through "standard output", blocks 254, 255), such as "Base good."

The Seismic Pavement Analyzer has great potential for commercialization. The device of the present invention is designed to meet the needs of pavement and maintenance engineers. The equipment may assist highway agencies in several ways. Its most obvious use is in network-level surveys as a routine maintenance tool. Also, highway agencies and research institutions may use the device as a high-level research tool for better understanding the behavior of pavements. The SPA provides comprehensive and accurate information at each test point.

Some of the unique and significant practical features of the system are:

1. Almost all the data reduction is carried out in the field; minimal data reduction is required in the office.
2. The flexible structure of the software allows easy upgrade of the data reduction or interpretive capabilities of the device by either the manufacturer or the potential owner.
3. Rapid graphical presentation of all the pavement parameters allows the testing program to be modified or extended in the field. The data may be transmitted over a cellular telephone to an experienced engineer in the headquarters, while a technician collects data in the field.
4. All the measured pavement parameters may be archived in a format that may be exported to a commercially available database or spreadsheet software; therefore, data reports may be produced quickly.
5. The SPA may be diagnosed, and recommendations for its repair may be given, over any cellular or public phone, minimizing down time of the equipment.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A device for seismically testing a multi-layer roadway surfacing, said surfacing comprising a paving layer, the device comprising:

a mobile support adapted to be moved across the surface of the paving layer;

a high-frequency seismic source mounted on said mobile support and adapted to be impacted on the paving layer so as to transmit a high-frequency seismic wave into said roadway surfacing;

a low-frequency seismic source mounted on said mobile support and adapted to be impacted on the paving layer so as to transmit a low-frequency seismic wave into said roadway surfacing;

a plurality of seismic transducers mounted on said mobile support and adapted to be coupled to the paving layer so as to detect said seismic waves following transmission through said roadway surfacing, wherein each said transducer is coupled to said mobile support through a separate pneumatic cylinder; and a computer electrically coupled to said transducers and seismic sources, said computer comprising:

means for initializing acquisition options to define measurement values for N seismic measurements to be made on said roadway surfacing to obtain selected surfacing parameters;

means for defining a bank of seismic transducers for each of N seismic measurements;

means for selecting a transducer bank based on said acquisition options;

means for receiving seismic data from said bank of seismic transducers;

means for processing said seismic data to obtain processed seismic data;

means for computing said selected surfacing parameters based on said processed seismic data;

means for evaluating said selected surfacing parameters to detect defects in said roadway surfacing; and means for diagnosing paving-layer-specific pavement distress precursors based on evaluated surfacing parameters.

2. The device of claim 1, wherein at least one of said transducers has an output responsive to frequency and at least one transducer has an output responsive to velocity.

3. The device of claim 2, wherein said transducers comprise:

at least one geophone; and at least one accelerometer.

4. The device of claim 1, wherein said high-frequency and low-frequency seismic sources each comprise a load cell for measuring the force of an impact of each said source.

5. The device of claim 1, further comprising temperature sensors coupled to said mobile support for detecting air temperature and paving layer temperature.

6. The apparatus of claim 1, wherein said diagnosing means comprises:

means for normalizing evaluated surfacing parameters based on design parameters for said roadway surfacing:

means for comparing said normalized surfacing parameters to a set of surfacing parameters having extreme values;

means for qualitatively evaluating said normalized surfacing parameters relative to said extreme values;

means for assigning a relative value to said normalized surfacing parameter based on said qualitative evaluation; and means for generating a message indicating said assigned relative value.

7. A seismic pavement analyzer, comprising:

a mobile support adapted to be moved across the surface of a pavement;

a high-frequency seismic source mounted on said support and adapted to repeatedly impact said pavement to generate a high-frequency seismic wave in said pavement, said high-frequency source comprising a load cell for measuring an impact force of said source;

a low-frequency seismic source mounted on said support and adapted to repeatedly impact said pavement to generate a low-frequency seismic wave in said pavement, said low-frequency source comprising a load cell for measuring an impact force of said source;

an actuator coupled to each of said seismic sources;

a plurality of transducers for receiving said seismic waves through said pavement, wherein each said transducer is coupled to said mobile support through a separate pneumatic cylinder, each of said cylinders being configured to actuate its corresponding transducer upon said pavement; and a computer electrically coupled to said transducers and seismic sources, comprising:

means for selecting a surfacing parameter to be measured;

means, responsive to said selection of a surfacing parameter, for selectively activating at least one of said actuators coupled to a seismic source associated with said selected surfacing parameter;

means for receiving seismic data from said transducers based on detected seismic waves;

means for processing said seismic data to obtain processed seismic data;

means for computing said selected surfacing parameter based on said processed seismic data;

means for evaluating said selected surfacing parameter to detect defects in said pavement; and means for diagnosing paving-layer-specific pavement distress precursors based on evaluated surfacing parameters.

8. The pavement analyzer of claim 7, wherein said transducers comprise:

at least one geophone for measuring particle velocity through said pavement in response to an impact by one of said seismic sources; and at least one accelerometer for measuring particle acceleration through said pavement in response to an impact by one of said seismic sources.

9. The pavement analyzer of claim 7, further comprising a pressurized air supply coupled to said pneumatic air cylinders.

10. The pavement analyzer of claim 9, said cylinders comprising:

an air chamber coupled to said air supply;

a spring for counterbalancing the weight of the transducer to which said cylinder is attached so that active pressure is required to actuate said accelerometer or geophone; and an electrically-controlled solenoid valve coupled to said computer and responsive to control signals from said computer.

11. The pavement analyzer of claim 9, said source actuators comprising:

an accumulator chamber coupled to said air supply;

an electrically-controlled solenoid valve coupled to said accumulator chamber and responsive to control signals from said computer, wherein said solenoid valve remains in a closed state to block air flow out of said accumulator chamber until a control signal is received from said computer;

a hammer cylinder coupled to said solenoid valve; and a spring disposed within said hammer cylinder.

12. The apparatus of claim 7, wherein said diagnosing means comprises:

means for normalizing evaluated surfacing parameters based on design parameters for said pavement;

means for comparing said normalized surfacing parameters to a set of surfacing parameters having extreme values;

means for qualitatively evaluating said normalized surfacing parameters relative to said extreme values;

means for assigning a relative value to said normalized surfacing parameter based on said qualitative evaluation; and means for generating a message indicating said assigned relative value.

13. A device for seismically testing a multi-layer roadway surfacing, said surfacing comprising a paving layer, the device comprising:

a mobile support adapted to be moved across the surface of the paving layer;

movable frame means mounted to the mobile support by an air cylinder;

a high-frequency seismic source mounted on said movable frame and adapted to be impacted on the paving layer so as to transmit a high-frequency seismic wave into said roadway surfacing;

a low-frequency seismic source mounted on said mobile support and adapted to be impacted on the paving layer so as to transmit a low-frequency seismic wave into said roadway surfacing;

a plurality of seismic transducers mounted on said mobile support and adapted to be coupled to the paving layer so as to detect said seismic waves following transmission through said roadway surfacing; and a computer electrically coupled to said transducers and seismic sources and operable to initiate said seismic waves and to receive and process the detected seismic signals to generate a shear modulus profile and dispersion curves for the layers of said roadway surfacing.

* * * * *